(12) United States Patent
Kura et al.

(10) Patent No.: US 6,806,024 B1
(45) Date of Patent: Oct. 19, 2004

(54) OXIME DERIVATIVES AND THE USE THEREOF AS PHOTOINITIATORS

(75) Inventors: Hisatoshi Kura, Hyogo (JP); Hitoshi Yamato, Hyogo (JP); Masaki Ohwa, Kobe (JP); Kurt Dietliker, Allschwil (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/914,433

(22) PCT Filed: Feb. 21, 2000

(86) PCT No.: PCT/EP00/01404

§ 371 (c)(1),
(2), (4) Date: Aug. 27, 2001

(87) PCT Pub. No.: WO00/52530

PCT Pub. Date: Sep. 8, 2000

(30) Foreign Application Priority Data

Mar. 3, 1999 (EP) ............................................. 99810180

(51) Int. Cl.$^7$ ............................................. G03F 7/004
(52) U.S. Cl. .................... 430/270.1; 430/922; 430/919; 522/57; 522/59; 522/65
(58) Field of Search ............................ 430/281.1, 922, 430/919; 522/57, 59, 65

(56) References Cited

U.S. PATENT DOCUMENTS

| | | | |
|---|---|---|---|
| 3,558,309 A | 1/1971 | Laridon et al. | 96/35.1 |
| 4,202,697 A | 5/1980 | Van Goethem et al. | 430/306 |
| 4,255,513 A | 3/1981 | Laridon et al. | 430/281 |
| 4,540,598 A | 9/1985 | Berner et al. | 427/54.1 |
| 4,590,145 A | 5/1986 | Itoh et al. | 430/281 |
| 5,019,482 A | 5/1991 | Ai et al. | 430/283 |
| 5,627,011 A | 5/1997 | Munzel et al. | 430/270.1 |
| 5,714,625 A | 2/1998 | Hada et al. | 558/437 |
| 5,759,740 A | 6/1998 | Munzel et al. | 430/270.1 |
| 6,004,724 A | * 12/1999 | Yamato et al. | 430/281.1 |

FOREIGN PATENT DOCUMENTS

| | | |
|---|---|---|
| DE | 19928742 | 12/1999 |
| DE | 19938796 | 2/2000 |
| EP | 0044115 | 1/1982 |
| EP | 0035291 | 5/1983 |
| GB | 2306958 | 5/1997 |
| GB | 2339571 | 2/2000 |
| GB | 2340494 | 2/2000 |
| WO | 98/10335 | 3/1998 |
| WO | 00/00869 | 1/2000 |
| WO | 00/10972 | 3/2000 |

OTHER PUBLICATIONS

Chem. Abstr. 96:52526 for Glas. Hem. Drus. Beograd (1981), 46(6), pp. 215–230.
H. Verter et al., Journal of Chemical and Engineering Data, vol. 9, No. 3, Jul. 1964, pp. 403–404.
S.–H. Zee et al., Journal of the Chinese Chemical Society, (1994), vol. 41, pp. 573–577.
Chem. Abstr. 109:83463 for JP 62273259 (1987).
Derwent Abstract 88–025703/04 for JP 2286961 (1987).
Derwent Abstract 87–288481/41 for JP 2201859 (1987).
Derwent Abstract 87–266739/38 for JP 2184056 (1987).
C. Groenenboom et al., Journal of Photochemistry and Photobiology A: Chemistry vol. 107, (1997), pp. 261–269.
W. J. Mijs et al., Journal of Coatings Technology vol. 55, No. 697, Feb. 1983, pp. 45–51.

* cited by examiner

*Primary Examiner*—Rosemary Ashton
(74) *Attorney, Agent, or Firm*—Tyler A. Stevenson

(57) ABSTRACT

Radically photopolymerizable compositions comprising (a) at least one ethylenically unsaturated photopolymerizable compound; (b) as photoinitiator, at least one compound of formulae (I, II, III, IV, V and/or VI), wherein m is 0 or 1; n is 0, 1, 2 or 3; x is 1 or 2; $R_1$ is inter alia phenyl, naphthyl, anthracyl or phenanthryl, a heteroaryl radical, $C_2$–$C_{12}$alkenyl, $C_4$–$C_8$cycloalkenyl, or $C_6$–$C_{12}$bicycloalkenyl; $R'_1$ is inter alia $C_2$–$C_{12}$alkylene, or phenylene; $R_2$ has one of the meanings of $R_1$ or inter alia is phenyl; y is 1 or 2; $R_3$ if x is 1 inter alia is $C_1$–$C_{18}$alkylsulfonyl, or phenyl-$C_1$–$C_3$alkylsulfonyl, $R_3$ if x is 2, is for example $C_2$–$C_{12}$alkylenedisulfonyl; $R_4$ and $R_5$ inter alia are hydrogen, halogen, or $C_1$–$C_8$alkyl; $R_6$, $R_7$, $R_8$ inter alia are hydrogen, $R_{26}$Y—, or phenyl; $R_9$ inter alia is $C_5$–$C_8$cycloalkyl, or phenyl; A is for example —S—, —O—, or —NR$_{10}$—; Q is $C_1$–$C_8$-alkylene optionally interrupted by —O—; X is —O— or —NR$_9$—; $R_{10}$ inter alia is hydrogen, or phenyl; and (c) at least one coinitiator; are especially suitable for the preparation of color filter systems.

15 Claims, No Drawings

OXIME DERIVATIVES AND THE USE THEREOF AS PHOTOINITIATORS

The invention relates to oxime derivatives and their use as photoinitiators in radically photopolymerizable compositions.

Oxime sulfonates are known as photoacid generators and accordingly are used in acid-curable compositions and in chemically amplified resists. In U.S. Pat. No. 4,540,598 surface-coating compositions based on photosensitive oxime sulfonates as photolatent acids and customary acid-curable resins are disclosed. In EP 571330 the use of α-(4-toluene-sulfonyloxyimino)-4-methoxybenzyl cyanide and α-(4-toluene-sulfonyloxyimino)-3-thienylmethyl cyanide as latent acid donors in positive and negative photoresists for wavelengths of 340–390 nm, especially those in the radiation region of the mercury i line (365 nm) is described. In GB 2306958 the use of oxime-sulfonates as latent acid donors in positive and negative photoresists for wavelengths between 180 and 600 nm, especially those in the radiation region beyond 390 nm is reported. In U.S. Pat. No. 5714625 non-aromatic α-(alkylsulfonyloxyimino)-1-cyclohexenylacetonitriles and α-(alkylsulfonyloxyimino)-1-cyclopentenylacetonitriles are disclosed. It is known that certain oxime carboxylate ester derivatives are photoinitiators as described in U.S. Pat. No. 3,558,309. Further disclosure of oxime carboxylate ester compounds is given for example in U.S. Pat. Nos. 4,255,513, 4,590,145, 4,202,697, Chemical Abstract No. 96:52526c, J. Chem. Eng. Data 9(3), 403–4 (1964), J. Chin. Chem. Soc. (Taipei) 41 (5) 573–8, (1994), JP 62-273259-A (=Chemical Abstract 109:83463w), JP 62-286961-A (=Derwent No. 88-025703/04), JP 62-201859-A (=Derwent No. 87-288481/41), JP 62-184056-A (=Derwent No. 87-266739/38), U.S. Pat. No. 5,019,482 and J. of Photochemistry and Photobiology A 107, 261–269 (1997).

The use of hydroximic acid ester sulfonates as thermal initiators for the polymerization of olefines in a temperature range from 50–350° C. is described in EP 35291. The activation with light of these compounds is, however, not disclosed. Further, α-oximinoacid ester sulfonates are mentioned as thermal acid generators for thermosetting coating compositions in EP 44115 and by W. J.-Mijis et al. in J. Coatings Technology 1983, 55, 45.

In radical photopolymerization technology there still exists a need for highly reactive, easy to prepare and easy to handle photoinitiator systems. In addition, such new photoinitiators must meet the high requirements of the industry regarding properties like, for example, thermal stability and storage stability.

Surprisingly, it has now been found that specific oxime derivatives of the formulae I, II, III, IV, V and/or VI, as described below, are especially suitable as photoinitiators for radical photo-polymerization in combination with coinitiators.

In accordance with the invention, the compounds of the formulae I, II, III, IV, V and/or VI can be used as radical photoinitiators for the photopolymerization of ethylenically unsaturated compounds or of mixtures which comprise such compounds.

The invention therefore relates to a radically photopolymerizable composition comprising
(a) at least one ethylenically unsaturated photopolymerizable compound,
(b) as photoinitiator, at least one compound of the formula I, II, III, IV, V and/or VI

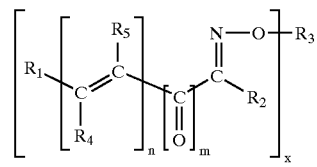

(I)

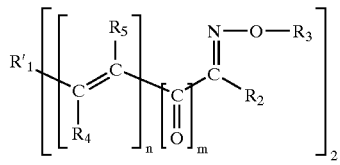

(II)

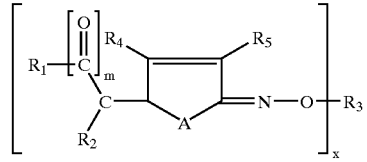

(III)

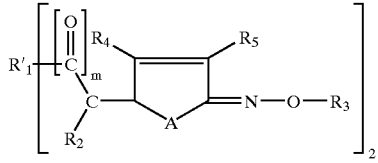

(IV)

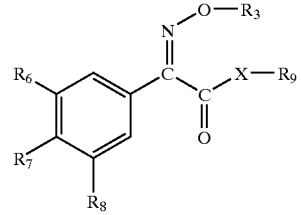

(V)

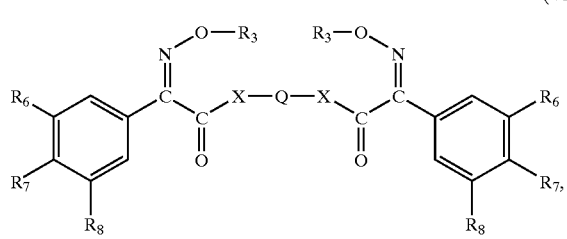

(VI)

wherein
m is 0 or 1;
n is 0, 1, 2 or 3;
x is 1 or 2;
$R_1$ is phenyl, phenyl which is substituted by one or more of the radicals $C_1$–$C_{12}$alkyl, $C_1$–$C_4$-haloalkyl, halogen, phenyl, $OR_{10}$, $NR_{11}R_{12}$, $SR_{13}$ and/or —S-phenyl, it being possible for the substituents $OR_{10}$, $SR_{13}$ and $NR_{11}R_{12}$ to form 5- or 6-membered rings, via the radicals $R_{10}$, $R_{11}$, $R_{12}$ and/or $R_{13}$, with further substituents on the phenyl ring or with one of the carbon atoms of the phenyl ring,
or $R_1$ is naphthyl, anthracyl or phenanthryl, the radicals naphthyl, anthracyl and phenanthryl being unsubstituted or substituted by $C_1$–$C_6$alkyl, phenyl, $OR_{10}$, $NR_{11}R_{12}$, $SR_{13}$ and/or —S-phenyl, it being possible for the substituents $OR_{10}$, $SR_{13}$ and $NR_{11}R_{12}$ to form 5- or 6-membered rings, via the radicals $R_{10}$, $R_{11}$, $R_{12}$ and /or $R_{13}$ with further substituents on the naphthyl, anthracyl or phenanthryl ring or with one of the carbon atoms of the naphthyl, anthracyl or phenanthryl ring, or $R_1$ is a heteroaryl radical which is unsubstituted or substituted by $C_1$–$C_6$alkyl, phenyl, $OR_{10}$, $NR_{11}R_{12}$, $SR_{13}$ and/or —S-phenyl, it being possible for the substituents $OR_{10}$, $SR_{13}$ and $NR_{11}R_{12}$ to form 5- or 6-membered rings, via the radicals $R_{10}$, $R_{11}$, $R_{12}$ and/or $R_{13}$ with further substituents on the heteroaryl ring or with one of the carbon atoms of the heteroaryl ring; or $R_1$ is $C_2$–$C_{12}$alkenyl, $C_4$–$C_8$cycloalkenyl, or $C_6$–$C_{12}$bicycloalkenyl, or, if m is zero, $R_1$ in the formula I additionally is benzoyl, 2-furoyl, 2-thiophenecarbonyl, 2-pyridinecarbonyl or 2-pyrrolecarbonyl, wherein the radicals benzoyl, 2-furoyl, 2-thiophenecarbonyl, 2-pyridinecarbonyl or 2-pyrrolecarbonyl are unsubstituted or substituted by one or more of the radicals $C_1$–$C_{12}$alkyl, $C_1$–$C_4$haloalkyl, halogen, phenyl, $OR_{10}$, $NR_{11}R_{12}$, $SR_{13}$ and/or —S-phenyl, it being possible for the substituents $OR_{10}$, $SR_{13}$ and $NR_{11}R_{12}$ to form 5- or 6-membered rings, via the radicals $R_{10}$, $R_{11}$, $R_{12}$ and/or $R_{13}$, with further substituents on the benzoyl, 2-furoyl, 2-thiophenecarbonyl, 2-pyridinecarbonyl or 2-pyrrolecarbonyl ring or with one of the carbon atoms of the benzoyl, 2-furoyl, 2-thiophenecarbonyl, 2-pyridinecarbonyl or 2-pyrrolecarbonyl ring;

or, if m is zero, n is 1 and simultaneously $R_5$ is phenyl which is unsubstituted or substituted by one or more $C_1$–$C_{12}$alkyl, $C_1$–$C_4$haloalkyl, halogen, phenyl, $OR_{10}$, $NR_{11}R_{12}$, $SR_{13}$ and/or —S-phenyl, $R_1$ in formula I additionally is hydrogen;

or, if m is 0 and n is 0, $R_1$ in formual I additionally is CN, hydrogen or $C_1$–$C_{12}$ alkyl, with the proviso that $R_1$ and $R_2$ are not simultaneously hydrogen or alkyl;

$R'_1$ is $C_2$–$C_{12}$alkylene, phenylene, naphthylene,

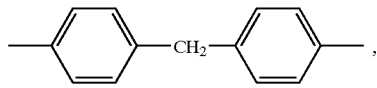

diphenylene or oxydiphenylene, these radicals are unsubstituted or substituted by $C_1$–$C_{12}$alkyl;

$R_2$ has one of the meanings of $R_1$ or is phenyl, CN-substituted phenyl, $C_2$–$C_6$alkanoyl, benzoyl which is unsubstituted or substituted by $C_1$–$C_6$alkyl, phenyl, $OR_{10}$, $SR_{13}$, $NR_{11}R_{12}$ and/or —S-phenyl, or $R_2$ is CN, phenoxycarbonyl, $NO_2$, $C_1$–$C_4$haloalkyl, $C_2$–$C_6$alkoxycarbonyl, $S(O)_y$—$C_1$–$C_6$alkyl, $S(O)_y$—$C_6$–$C_{12}$aryl, $C_1$–$C_{12}$alkyl-substituted $S(O)_y$—$C_6$–$C_{12}$aryl, $SO_2O$-$C_1$–$C_6$alkyl, $SO_2O$-$C_6$–$C_{10}$aryl, diphenylphosphinoyl or $NHCONH_2$, or, if m is 1, $R_1$ and $R_2$ together with the CO group may form a 5- or 6-membered ring which is unsubstituted or substituted by $C_1$–$C_6$alkyl, phenyl, $OR_{10}$, $SR_{13}$, $NR_{11}R_{12}$ and/or —S-phenyl, said ring may additionally be interrupted by —O—, —S—, —N($R_{11}$)— and/or by CO, and to said ring may be fused one or more benzo radicals;

y is 1 or 2;

$R_3$ if x is 1 is $C_1$–$C_{18}$alkylsulfonyl, phenyl-$C_1$–$C_3$alkylsulfonyl, camphorylsulfonyl, $C_1$–$C_{10}$haloalkylsulfonyl, phenylsulfonyl, naphthylsulfonyl, anthracylsulfonyl or phenanthrylsulfonyl, wherein the groups phenyl, naphthyl, anthracyl and phenanthryl of the radicals phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, $NO_2$, $C_1$–$C_{16}$alkyl, phenyl, $C_1$–$C_4$alkylthio, $OR_{10}$, $COOR_{13}$, $C_1$–$C_4$alkyl-OCO—, $R_{13}OSO_2$— and/or —$NR_{11}R_{12}$; or $R_3$ is $C_2$–$C_6$haloalkanoyl, halobenzoyl, or a group

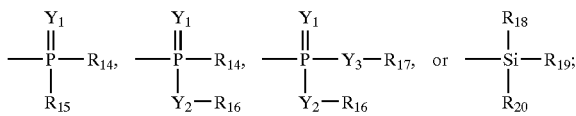

$R_3$ if x is 2, is $C_2$–$C_{12}$alkylenedisulfonyl, phenylenedisulfonyl, naphthylenedisulfonyl,

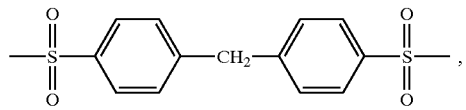

diphenylenedisulfonyl, or oxydiphenylenedisulfonyl, wherein the groups phenylene, naphthylene,

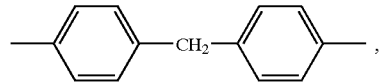

diphenylene and oxydiphenylene of the radicals phenylenedisulfonyl, naphthylenedisulfonyl,

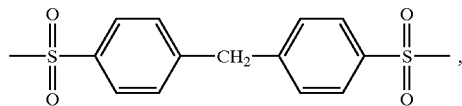

diphenylenedisulfonyl or oxydiphenylenedisulfonyl are unsubstituted or substituted by $C_1$–$C_{12}$alkyl;

$R_4$ and $R_5$ are independently of each other hydrogen, halogen, $C_1$–$C_8$alkyl, $C_1$–$C_6$alkoxy, $C_1$–$C_4$haloalkyl, CN, $NO_2$, $C_2$–$C_6$alkanoyl, benzoyl, phenyl, —S-phenyl, $OR_{10}$, $SR_{13}$, $NR_{11}R_{12}$, $C_2$–$C_6$alkoxycarbonyl, phenoxycarbonyl, $S(O)_yC_1$–$C_6$alkyl, $S(O)_yC_6$–$C_{12}$aryl, $C_1$–$C_{12}$alkyl-substituted $S(O)_yC_6$–$C_{12}$aryl, $SO_2O$—$C_1$–$C_6$alkyl, $SO_2O$—$C_6$–$C_{10}$aryl or $NHCONH_2$, or $R_4$ and $R_5$ together are a direct bond or —$C(R_{21})$=$C(R_{22})$—$C(R_{23})$=$C(R_{24})$—;

$R_6$, $R_7$, $R_8$ independently of one another are hydrogen, $R_{26}Y$—, phenyl optionally substituted by $C_1$–$C_4$alkyl or $C_1$–$C_4$alkyl-Y; or $R_6$, $R_7$ and $R_8$ are $C_1$–$C_8$ alkyl optionally substituted by halogen, OH, $OR_{25}$, $COOR_{25}$, or $C_1$–$C_4$-alkyl-COO—, or optionally interrupted by one or more —O—;

or $R_6$ and $R_7$ together with the atoms to which they are bound form a 5- or 6-membered saturated or unsaturated ring which is unsubstituted or substituted by one or more $C_1$–$C_4$alkyl and which ring optionally is interrupted by one or more Y or to which ring other rings are condensed;

$R_9$ is $C_5$–$C_8$cycloalkyl, phenyl, optionally substituted by $C_1$–$C_4$alkyl; or is $C_1$–$C_{12}$alkyl, optionally substituted by halogen, OH, or $OR_{25}$, or optionally interrupted by one or more —O—;

A is —S—, —O—, —NR$_{10}$—, or a group of formula A1, A2, A3 or A4

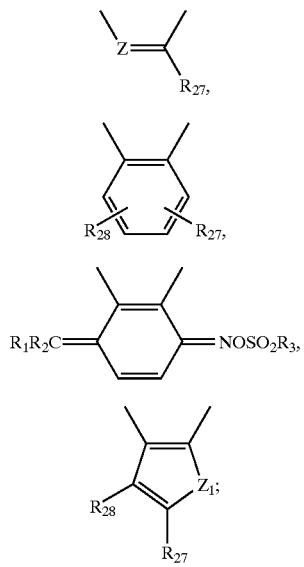

(A1)
(A2)
(A3)
(A4)

Q is $C_1$–$C_8$-alkylene optionally interrupted by one or more —O—;

X is —O— or —NR9—

Y, Y$_1$, Y$_2$ and Y3 independently of one another are —O— or —S—;

Z is —CR$_{28}$— or —N—; and

Z$_1$ is —CH$_2$—, —S—, —O— or —NR$_{10}$—;

R$_{10}$ is hydrogen, phenyl, $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by C2–$C_6$-alkanoyl or R$_{10}$ is $C_2$–$C_{12}$alkyl interrupted by one or more —O—, said interrupted $C_2$–$C_{12}$alkyl is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl;

R$_{11}$ and R$_{12}$ independently of one another are hydrogen, $C_1$–$C_{12}$alkyl which is unsubstituted or substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl; or R$_1$, and R$_{12}$ are $C_2$–$C_{12}$alkyl interrupted by one or more —O—, said interrupted $C_2$–$C_{12}$alkyl is unsubstituted or substituted by OH, $C_1$–$C_4$alkoxy, $C_1$–$C_{12}$alkyl-sulfonyl, phenylsulfonyl, (4-methylphenyl)sulfonyl and/or $C_1$–$C_6$alkanoyl; or R$_{11}$ and R$_{12}$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or R$_{11}$, and R$_{12}$, together with the nitrogen atom to which they are bonded, form a 5-, 6- or 7-membered ring which may be interrupted by —O— or by —NR$_{10}$—;

R$_{13}$ is $C_1$–$C_{12}$alkyl which is unsubstituted or substituted by OH and/or $C_1$–$C_4$alkoxy or R$_{13}$ is $C_2$–$C_{12}$alkyl interrupted by one or more —O—, said interrupted $C_2$–$C_{12}$alkyl is unsubstituted or substituted by OH and/or $C_1$–$C_4$alkoxy;

R$_{14}$ and R$_{15}$ independently of one another are $C_1$–$C_6$alkyl which is unsubstituted or substituted by halogen or phenyl or R$_{14}$ and R$_{15}$ are phenyl which is unsubstituted or substituted by $C_1$–$C_4$alkyl or halogen;

R$_{16}$ and R$_{17}$ independently of one another have one of the meanings of R$_{14}$, or R$_{16}$ and R$_{17}$ together are 1,2-phenylene or $C_2$–$C_6$alkylene which is unsubstituted or substituted by $C_1$–$C_4$-alkyl or halogen;

R$_{18}$, R$_{19}$, and R$_{20}$ independently of each other are $C_1$–$C_6$alkyl which is unsubstituted or substituted by halogen, or R$_{18}$, R$_{19}$ and R$_{20}$ are phenyl which is unsubstituted or substituted by $C_1$–$C_4$alkyl or halogen, or R$_{19}$ and R$_{20}$ together are 2,2'-biphenylene or $C_2$–$C_6$alkylene which is unsubstituted or substituted by $C_1$–$C_4$alkyl or halogen;

R$_{21}$, R$_{22}$, R$_{23}$ and R$_{24}$ independently of each other are hydrogen, $C_1$–$C_4$alkyl, halogen, phenyl, OR$_{10}$, SR$_{13}$, NR$_{11}$R$_{12}$, —S-phenyl, $C_2$–$C_6$alkoxycarbonyl, phenoxycarbonyl, CN, NO$_2$, $C_1$–$C_4$haloalkyl, S(O)$_y$$C_1$–$C_6$alkyl, S(O)$_y$$C_6$–$C_{12}$aryl, $C_1$–$C_{12}$alkyl-substituted S(O)$_y$$C_6$–$C_{12}$aryl, SO$_2$O—$C_1$–$C_6$alkyl, SO$_2$O—$C_6$–$C_{10}$aryl or NHCONH$_2$;

R$_{25}$ is $C_1$–$C_8$ alkyl optionally substituted by halogen, OH, or $C_1$–$C_4$-alkoxy or optionally interrupted by one or more —O—;

R$_{26}$ is phenyl, optionally substituted by $C_1$–$C_4$alkyl or $C_1$–$C_4$alkyl-Y; or is $C_1$–$C_8$ alkyl optionally substituted by halogen, OH, OR$_{25}$, COOR$_{25}$, or $C_1$–$C_4$alkyl-COO—,or optionally interrupted by one or more —O—;

R$_{27}$ and R$_{28}$ independently of one another have one of the meanings given for R$_4$, or R$_{27}$ and R$_{28}$ together are —CO—NR$_{10}$CO—, or —C(R$_{21}$)=C(R$_{22}$)-C(R$_{23}$)=C (R$_{24}$)—; and (c) at least one coinitiator.

$C_1$–$C_{12}$alkyl is linear or branched and is, for example, $C_1$–$C_8$-, $C_1$–$C_6$- or $C_1$–$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl or dodecyl, especially $C_1$–$C_6$alkyl, preferably $C_1$–$C_4$alkyl, such as methyl, isopropyl or butyl. Of interest are, for example, $C_1$–$C_8$-, especially $C_1$–$C_6$-, preferably $C_1$–$C_4$-alkyl, such as methyl or butyl.

$C_2$–$C_{12}$alkyl, which is interrupted once or several times by —O— or by —NR$_6$—, is interrupted, for example, from one to five times, for example from one to three times or once or twice, by —O— or —NR$_6$—. The interrupting O-atoms in the chain are non-successive. This results in structural units as for example: —O(CH$_2$)$_2$OCH$_3$, —O(CH$_2$CH$_2$O)$_2$CH$_2$CH$_3$, —CH$_2$—O—CH$_3$, —CH$_2$CH$_2$—O—CH$_2$CH$_3$, —[CH$_2$CH$_2$O]y—CH$_3$, wherein y is an integer of 1–5, —(CH$_2$CH$_2$O)$_5$CH$_2$CH$_3$, —CH$_2$—CH(CH$_3$)—O—CH$_2$—CH$_2$CH$_3$ or —CH$_2$—CH(CH$_3$)—O—CH$_2$—CH$_3$.

If alkyl groups are interrupted one or more times by Y they are interrupted, for example, from one to five times, for example from one to three times or once or twice, by Y. If Y is —O—, the interrupting O-atoms in the chain are non-successive.

$C_2$–$C_{12}$alkenyl radicals may be mono or polyunsaturated, linear or branched and are for example $C_2$–$C_8$-, $C_2$–$C_6$- or $C_2$–$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_4$–$C_8$-cycloalkenyl, may have one or more double bonds and is for example $C_4$–$C_6$-cycloalkenyl or $C_6$–$C_8$-cycloalkenyl. Examples are cyclobutenyl, cyclopentenyl, cyclohexenyl or cyclooctenyl, especially cyclopentenyl and cyclohexenyl, preferably cyclohexenyl.

$C_6$–$C_{12}$bicycloalkenyl refers to a bicyclic alkenyl group, which may possess one or more double bonds and wherein the double bonds are either situated in the same ring, but may also be situated in both rings. If several double bonds are present in the bicyclus, the double bonds are conjugated or non-conjugated, preferably the double bonds are conjugated. At least one of the double bonds of the bicycloalkenyl radical is conjugated with the double bond of formula I, II which is substituted by the radicals $R_4$ and $R_5$. Examples are bicyclo-[4.2.4]dodec-3,7-dien-5-yl, bicyclo[4.2.4]dodec-3-en-5-yl, bicyclo[4.2.4]dodec-4-en-6-yl, bicyclo[4.2.3]-non-3-en-5-yl, bicyclo[4.2.3)-non-4-en-6-yl, bicyclo[4.2.3]-non-7-en-8yl, bicyclo-[4.2.3]-non-8-en-7-yl, wherein the examples are referring to the following numbering

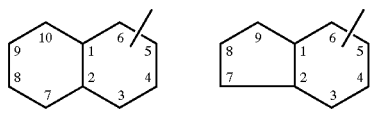

$C_1$–$C_{12}$Alkylene and $C_1$–$C_8$alkylene are linear or branched and are, for example, $C_1$–$C_6$-, $C_1$–$C_4$-, $C_2$–$C_8$-, $C_2$–$C_6$- or $C_2$–$C_4$-alkylene. Examples are methylene, ethylene, propylene, butylene, pentylene, hexylene, heptylene, octylene, nonylene, decylene, undecylene and dodecylene, especially $C_1$–$C_6$alkylene, preferably $C_1$–$C_4$alkylene, such as methylene or butylene.

$C_2$–$C_{12}$alkylenedisulfonyl accordingly is an alkylene radical as indicated above, which at both "yl"-moieties bears a sulfonyl group. Examples are —$SO_2$—$(CH_2CH_2)_z$—$SO_2$—, with z=1–6, e.g. —$SO_2$—$CH_2CH_2$—$SO_2$—, or —$SO_2$—$CH(CH_3)CH_2$—$SO_2$—.

Phenylenedisulfonyl, diphenylenedisulfonyl and oxydiphenylendisulfonyl also bear the sulfonyl groups at the "yl" moiety. Accordingly, resulting structures are

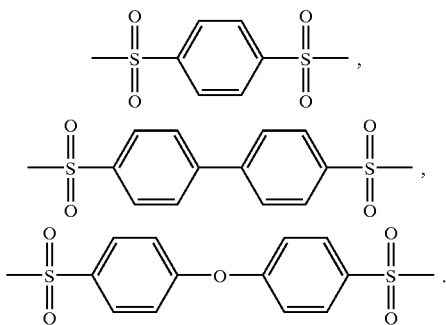

Substituted phenyl carries from one to five, for example one, two or three, especially one or two, substituents on the phenyl ring. The substitution is, for example in the 2-, 3-, 4-, 6-, 3,4-, 2,6-, 2,4-, 2,4,6- or 3,4,5-position of the phenyl ring. When the radicals naphthyl, phenanthryl, heteroaryl and anthracyl are substituted by one or more radicals, they are, for example, mono- to penta-substituted, for example mono-, di- or tri-substituted, especially mono- or di-substituted.

When $R_1$ is a phenyl radical substituted by $OR_{10}$, $NR_{11}R_{12}$ and/or by $SR_{13}$ and the substituents $OR_{10}$, $NR_{11}R_{12}$ and $SR_{13}$ form 5- or 6-membered rings, via the radicals $R_{10}$, $R_{11}$, $R_{12}$ or $R_{13}$, with other substituents on the phenyl ring or with one of the carbon atoms of the phenyl ring, for example the following structural units are obtained

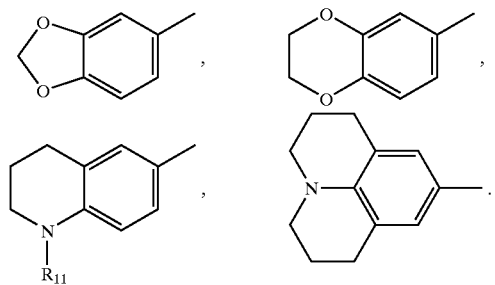

In the present application, the term "heteroaryl" denotes unsubstituted and substituted radicals, for example 2-thienyl,

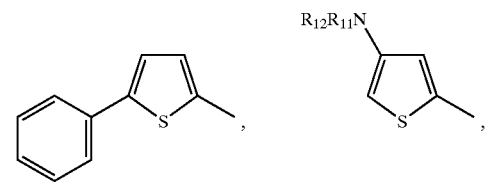

wherein $R_{11}$ and $R_{12}$ are as defined above, thianthrenyl, isobenzofuranyl, xanthenyl, phenoxanthiinyl,

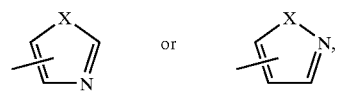

wherein X is S, O or $NR_9$ and $R_9$ is as defined above. Examples thereof are pyrazolyl, thiazolyl, oxazolyl, isothiazolyl or isoxazolyl. Also included are, for example, furyl, pyrrolyl, 1,2,4-triazolyl,

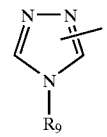

or 5-membered ring heterocycles having a fused-on aromatic group, for example benzimidazolyl, benzothienyl, benzofuranyl, benzoxazolyl and benzothiazolyl.

Other examples of "heteroaryls" are pyridyl, especially 3-pyridyl,

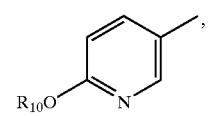

wherein $R_{10}$ is as defined above, pyrimidinyl, pyrazinyl, 1,3,5-triazinyl, 2,4-, 2,2- or 2,3-diazinyl, indolizinyl, isoindolyl, indolyl, indazolyl, purinyl, isoquinolyl, quinolyl, phenoxazinyl or phenazinyl. In this Application, the term "heteroaryl" also denotes the radicals thioxanthyl, xanthyl,

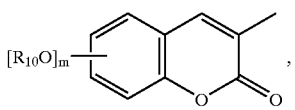

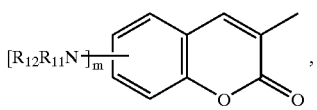

wherein $R_{10}$, $R_{11}$, $R_{12}$ and m are as defined above,

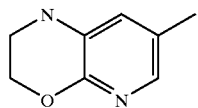

or anthraquinonyl. Each of the heteroaryls may carry the substituents indicated above or in claim 1.

When $R_1$ and $R_2$ together with the CO group form a 5- or 6-membered ring, it is, for example, a cyclopentanone, or cyclohexanone ring. There may be fused to that ring, for example, also benzo, naphtho, anthraceno, phenanthreno or heteroaryl radicals, thereby forming structures such as

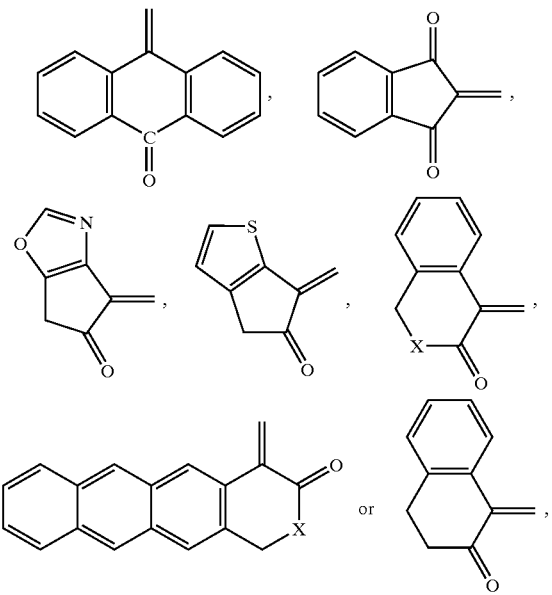

wherein X is S, or $NR_9$ and $R_9$ is as defined above, and in which structures the aromatic rings may carry further substituents as definded above and in claim 1.

Apparently these structures are not strictly "$R_1$ and $R_2$ together", but are partial illustrations of the final compounds.

They are, for example, also benzoquinone, naphthoquinone or anthraquinone radicals.

$C_1$–$C_6$Alkanoyl is, for example, formyl, acetyl, propionyl, butanoyl or hexanoyl, especially acetyl.

$C_1$–$C_{12}$Alkoxy is a linear or branched radical and is $C_1$–$C_8$-, $C_1$–$C_6$-, $C_1$–$C_4$alkoxy, for methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy, octyloxy, nonyloxy, decyloxy or dodecyloxy, especially methoxy, ethoxy, propoxy, isopropoxy, n-butyloxy, secbutyloxy, iso-butyloxy or tert-butyloxy, preferably methoxy. $C_1$–$C_6$alkoxy is has the same meanings as given above up to the corresponding number of C-atoms.

$C_2$–$C_6$Alkoxycarbonyl is ($C_1$–$C_5$alkyl)-O—C(O)—, wherein $C_1$–$C_5$alkyl is as defined above up to the appropriate number of carbon atoms. Examples are methoxycarbonyl, ethoxycarbonyl, propoxycarbonyl, butoxycarbonyl or pentyloxycarbonyl, wherein the alkyl radicals having more than two carbon atoms are linear or branched.

$C_1$–$C_4$haloalkyl is $C_1$–$C_4$alkyl mono- or poly-substituted by halogen, $C_1$–$C_4$alkyl is as defined above. There are, for example, from one to three or one or two halogen substituents at the alkyl radical. Examples are chloromethyl, trichloromethyl, trifluoromethyl or 2-bromopropyl, especially trifluoromethyl or trichloromethyl.

$C_2$–$C_6$haloalkanoyl is ($C_1$–$C_5$haloalkyl)-C(O)—, wherein $C_1$–$C_5$haloalkyl is linear or branched $C_1$–$C_5$alkyl mono- or poly-substituted by halogen. Examples are chloroacetyl, trichloroacetyl, trifluoroacetyl, pentafluoropropionyl, perfluorooctanoyl, or 2-bromopropionyl, especially trifluoroacetyl or trichloroacetyl.

Halobenzoyl is benzoyl which is mono- or poly-substituted by halogen and/or $C_1$–$C_4$haloalkyl, wherein $C_1$–$C_4$haloalkyl is as defined above. Examples are pentafluorobenzoyl, trichlorobenzoyl, trifluoromethylbenzoyl, especially pentafluorobenzoyl.

Halogen is fluorine, chlorine, bromine or iodine, especially chlorine or fluorine, preferably fluorine.

In a group $S(O)_y$—$C_6$–$C_{10}$aryl which is unsubstituted or substituted by $C_1$–$C_{12}$alkyl, the aryl radical is, for example, phenyl, tolyl, dodecylphenyl or 1- or 2-naphthyl.

Phenyl-$C_1$–$C_3$alkyl is, for example, benzyl, 2-phenylethyl, 3-phenylpropyl, α-methylbenzyl or α,α-dimethylbenzyl, especially benzyl.

Oxydiphenylene

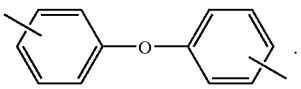

Dialkoxyphosphinoxyl is for example di($C_1$–$C_{12}$alkoxy)-phosphinoyl, and corresponds also to the different meanings for "$C_1$–$C_{12}$alkoxy" given above. Preferred is diethoxyphosphinoyl.

When $R_{11}$ and $R_{12}$ together with the nitrogen atom to which they are bonded form a 5-, 6- or 7-membered ring that may be interrupted by —O— or by —$NR_{10}$—, for example the following structures are obtained

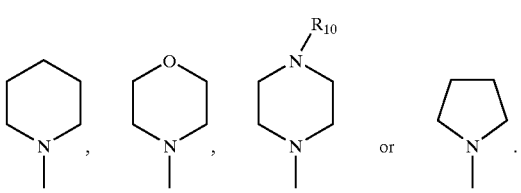

When $R_4$ and $R_5$ together are —$(CR_{21})$=$C(R_{22})$—$C(R_{23})$=$C(R_{24})$— the following structures are formed

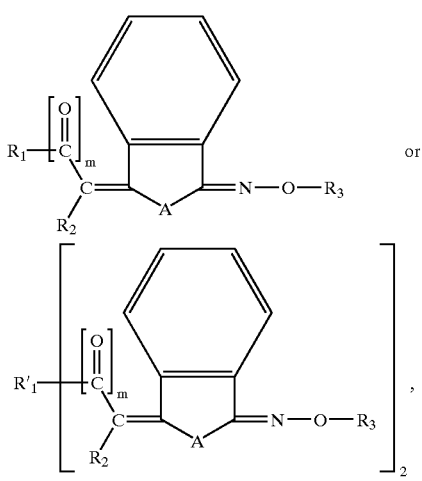

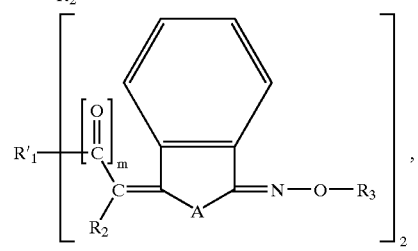

wherein $R_1$, $R_2$, m, $R_3$, $R'_1$ and A are as defined above or in claim 1.

When $R_6$ and $R_7$ together with the atoms to which they are bound form a 5- or 6-membered saturated or unsaturated ring which is unsubstituted or substituted by one or more $C_1$–$C_4$alkyl and which ring optionally is interrupted by one or more Y or to which ring other rings are condensed the following structures can be formed:

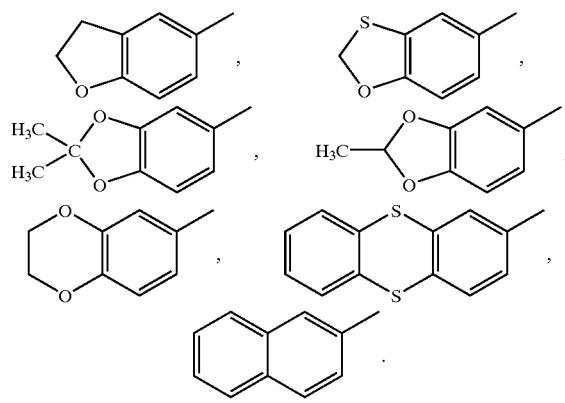

One or more substituents $C_1$–$C_4$alkyl are for example 1 to 3, 1 or 2, in particular 1 substituent. Rings which optionally are condensed to the rings formed by $R_6$ and $R_7$ are for example phenyl rings.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

Preference is given to compositions wherein the compounds of formula I, II, III, IV, V and VI, $R_3$ if x is 1 is $C_1$–$C_{18}$alkylsulfonyl, phenyl-$C_1$–$C_3$alkylsulfonyl, camphorylsulfonyl, $C_1$–$C_{10}$haloalkylsulfonyl, phenylsulfonyl, naphthylsulfonyl, anthracylsulfonyl or phenanthrylsulfonyl, wherein the groups phenyl, naphthyl, anthracyl and phenanthryl of the radicals phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, $NO_2$, $C_1$–$C_{16}$alkyl, phenyl, $C_1$–$C_4$alkylthio, $OR_{10}$, $COOR_{13}$, $C_1$–$C_4$alkyl-OCO—, $R_{13}OSO_2$—and/or —$NR_{11}R_{12}$; or $R_3$ is a group

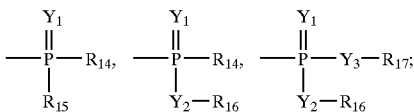

$R_3$ if x is 2 is $C_2$–$C_{12}$alkylenedisulfonyl, phenylenedisulfonyl, naphthylenedisulfonyl,

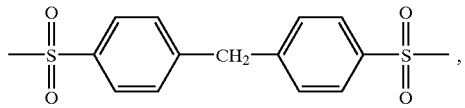

diphenylenedisulfonyl, or oxydiphenylenedisulfonyl, wherein the groups phenylene, naphthylene,

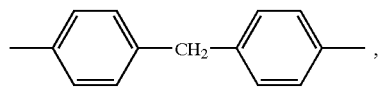

diphenylene and oxydiphenylene of the radicals phenylenedisulfonyl, naphthylenedisulfonyl,

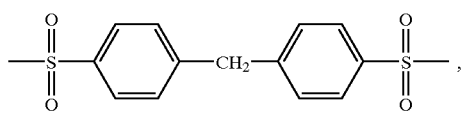

diphenylenedisulfonyl, or oxydiphenylenedisulfonyl are unsubstituted or substituted by $C_1$–$C_{12}$alkyl; and $Y_1$, $Y_2$ and $Y_3$ independently of each other are —O— or —S—.

Further compositions of interest are those wherein component (b) is a compound of formula I, II or III, wherein m is zero.

Interesting are compositions comprising as component (b) a compound of formula Ia or IIa

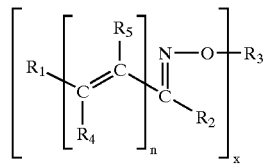

(Ia)

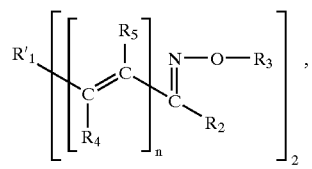

(IIa)

wherein n is 0 or 1;

$R_1$, $R'_1$, $R_2$, $R_3$, $R_4$, $R_5$ and x are as defined above.

Further preferred is a composition, wherein component (b) is a compound of formula IIIa

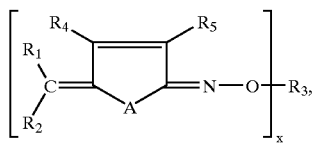
(IIIa)

wherein $R_1$, $R_2$, $R_3$, $R_4$, $R_5$, A and x are as defined above.

wherein

Special mention should be made of compositions wherein wherein component (b) is a compound of formula I, III, V or VI wherein n and m independently of one another are 0 or 1;

x is 1;

$R_1$ is phenyl which unsubstituted or substituted once or twice by $C_1$–$C_4$alkyl, halogen, $OR_{10}$ or $SR_{13}$;

$R_1'$ is phenylene;

$R_2$ is $C_2$–$C_6$alkoxycarbonyl, or CN;

$R_3$ is $C_1$–$C_8$alkylsulfonyl, or phenylsulfonyl, wherein the group phenyl of the radical phenylsulfonyl is unsubstituted or substituted by $C_1$–$C_8$alkyl or $OR_{10}$; or $R_3$ is a group,

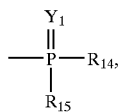 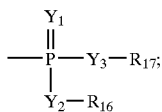

$R_4$ and $R_5$ independently of one another are hydrogen or $C_1$–$C_8$alkyl;

$R_6$ is hydrogen;

$R_{12}$ is hydrogen or $C_1$–$C_4$alkyl;

$R_{10}$ and $R_{13}$ independently of one another are $C_1$–$C_4$alkyl;

A is —S—;

$Y_1$, $Y_2$ and $Y_3$ are —O—;

X is —O— or —$NR_9$—;

Q is $C_1$–$C_8$-alkylene optionally interrupted by —O—;

$R_{14}$ and $R_{15}$ independently of one another are phenyl or $C_1$–$C_4$alkyl-substituted phenyl;

$R_{16}$ and $R_{17}$ independently of one another are $C_1$–$C_4$alkyl.

The invention relates also the novel oxime derivatives of formula V or VI

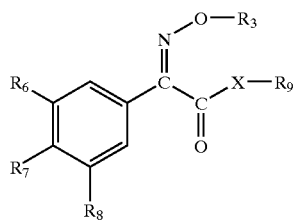
(V)

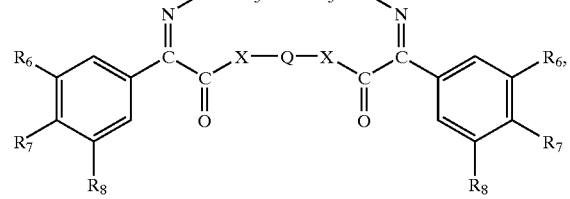
(VI)

wherein $R_3$ is $C_1$–$C_{18}$alkylsulfonyl, phenyl-$C_1$–$C_3$alkylsulfonyl, camphorylsulfonyl, $C_1$–$C_{18}$haloalkyl-sulfonyl, phenylsulfonyl, naphthylsulfonyl, anthracylsulfonyl or phenanthrylsulfonyl, wherein the groups phenyl, naphthyl, anthracyl and phenanthryl of the radicals phenyl-$C_1$–$C_3$alkylsulfonyl, phenylsulfonyl, naphthylsulfonyl, anthracylsulfonyl and phenanthryl-sulfonyl are unsubstituted or substituted by one or more halogen, $C_1$–$C_4$haloalkyl, CN, $NO_2$, $C_1$–$C_{16}$alkyl, phenyl, $C_1$–$C_4$alkylthio, $OR_{10}$, $COOR_{13}$, $C_1$–$C_4$alkyl-OCO—, $R_{13}OSO_2$- and/or —$NR_{11}R_{12}$; or $R_3$ is $C_2$–$C_6$haloalkanoyl, halobenzoyl, or a group

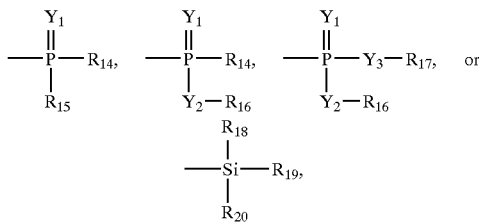

$R_6$, $R_7$, $R_8$ independently of each other are hydrogen, $R_{26}Y$—, phenyl optionally substituted by $C_1$–$C_4$alkyl or $C_1$–$C_4$alkyl-Y—; or $R_6$, $R_7$ and $R_8$ are $C_1$–$C_8$ alkyl optionally substituted by halogen, OH, $OR_{25}$, $COOR_{25}$, or $C_1$–$C_4$-alkyl-COO—, or optionally interrupted by one or more —O—;

or $R_6$ and $R_7$ together with the atoms to which they are bound form a 5- or 6-membered saturated or unsaturated ring which is unsubstituted or substituted by one or more $C_1$–$C_4$alkyl and which ring optionally is interrupted by one or more Y or to which ring other rings are condensed;

Q is $C_1$–$C_8$-alkylene optionally interrupted by one or more —O—;

X is —O— or —$NR_9$—;

Y, $Y_1$, $Y_2$ and $Y_3$ independently of each other are —O— or —S—;

$R_9$ is $C_5$–$C_8$cycloalkyl, phenyl, optionally substituted by $C_1$–$C_4$alkyl; or is $C_1$–$C_{12}$alkyl, optionally substituted by halogen, OH, or $OR_{25}$, or optionally interrupted by one or more —O—;

$R_{25}$ is $C_1$–$C_8$alkyl optionally substituted by halogen, OH, or $C_1$–$C_4$-alkoxy or optionally interrupted by one or more —O—;

$R_{26}$ is phenyl, optionally substituted by $C_1$–$C_4$alkyl or $C_1$–$C_4$alkyl-Y; or is $C_1$–C8 alkyl optionally substituted by halogen, OH, $OR_{25}$, $COOR_{25}$, or $C_1$–$C_4$alkyl—COO—,or optionally interrupted by one or more —O—;

with the proviso that if $R_3$ is $CH_3C_6H_4SO_2$—, $R_6$, $R_7$ and $R_8$ are hydrogen and X is oxygen, $R_9$ is not methyl or ethyl;

$R_{10}$ is hydrogen, phenyl, $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$-alkanoyl or $R_{10}$ is $C_2$–$C_{12}$alkyl interrupted by one or more —O—, said interrupted $C_2$–$C_{12}$alkyl is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl;

$R_{11}$ and $R_{12}$ independently of one another are hydrogen, $C_1$–$C_{12}$alkyl which is unsubstituted or substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl; or $R_{11}$ and $R_{12}$ are $C_2$–$C_{12}$alkyl interrupted by one or more —O—, said interrupted $C_2$–$C_{12}$alkyl is unsubstituted or substituted by OH, $C_1$–$C_4$alkoxy, $C_1$–$C_{12}$alkyl-sulfonyl, phenylsulfonyl, (4-methylphenyl)sulfonyl and/or $C_1$–$C_6$alkanoyl; or $R_{11}$ and $R_{12}$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_{11}$ and $R_{12}$, together with the nitrogen atom to which they are bonded, form a 5-, 6- or 7-membered ring which may be interrupted by —O— or by —$NR_{10}$—;

$R_{13}$ is $C_1$–$C_{12}$alkyl which is unsubstituted or substituted by OH and/or $C_1$–$C_4$alkoxy or is $C_2$–$C_{12}$alkyl interrupted by one or more —O—, said interrupted $C_2$–$C_{12}$alkyl is unsubstituted or substituted by OH and/or $C_1$–$C_4$alkoxy;

$R_{14}$ and $R_{15}$ independently of one another are $C_1$–$C_6$alkyl which is unsubstituted or substituted by halogen, or are phenyl which is unsubstituted or substituted by $C_1$–$C_4$alkyl or halogen;

$R_{16}$ and $R_{17}$ independently of one another have one of the meanings of $R_{14}$; or $R_{16}$ and $R_{17}$ together are 1,2-phenylene or $C_2$–$C_6$alkylene which is unsubstituted or substituted by $C_1$–$C_4$alkyl or halogen;

$R_{18}$, $R_{19}$ and $R_{20}$ independently of each other are $C_1$–$C_6$alkyl, which is unsubstituted or substituted by halogen: or are phenyl which is unsubstituted or substituted by $C_1$–$C_4$alkyl or halogen, or $R_{19}$ and $R_{20}$ together are 2,2'-biphenylene or $C_2$–$C_6$alkylene which is unsubstituted or substituted by $C_1$–$C_4$alkyl or halogen.

Preference is given especially to compounds of formula V and VI wherein $R_3$ is unsubstituted or fluorine-substituted $C_1$–$C_4$-alkylsulfonyl, unsubstituted or fluorine-substituted phenylsulfonyl, $C_1$–$C_{12}$-alkylphenylsulfonyl or a group

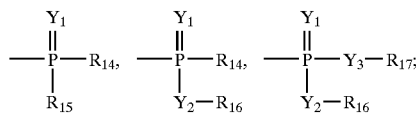

$R_6$, $R_7$ and $R_8$ independently of each other are hydrogen, $R_{26}Y$—, phenyl optionally substituted by $C_1$–$C_4$alkyl or $C_1$–$C_4$alkyl-Y—; or $R_6$, $R_7$ and $R_8$ are $C_1$–$C_8$ alkyl optionally substituted by OH, $OR_{25}$, or $COOR_{25}$, or optionally interrupted by one or more —O—;

or $R_6$ and $R_7$ together with the atoms to which they are bound form a 5- or 6-membered saturated or unsaturated ring which is unsubstituted or substituted by one or more $C_1$–$C_4$alkyl and which ring optionally is interrupted by one or more Y or to which ring other rings are condensed;

Q is $C_1$–$C_8$-alkylene optionally interrupted by one or more —O—;

Y is —O— or —S—;

$Y_1$, $Y_2$ and $Y_3$ are —O—;

X is —O— or —$NR_9$—;

$R_9$ is cyclohexyl, phenyl, optionally substituted by $C_1$–$C_4$alkyl; or is $C_1$–$C_{12}$alkyl, optionally substituted by OH, or $OR_{25}$, or optionally interrupted by one or more —O—;

$R_{25}$ is $C_1$–$C_8$alkyl optionally substituted by OH or $C_1$–$C_4$-alkoxy or optionally interrupted by one or more —O—;

$R_{26}$ is phenyl, optionally substituted by $C_1$–$C_4$alkyl or $C_1$–$C_4$alkyl-Y; or is $C_1$–$C_8$alkyl optionally substituted by OH, $OR_{25}$, or $COOR_{25}$; or optionally interrupted by one or more —O—;

with the proviso that if $R_3$ is $CH_3C_6H_4SO_2$—, $R_6$, $R_7$ and R8 are hydrogen and X is oxygen, $R_9$ is not methyl or ethyl.

Especially preferred are compounds of formula V or VI, wherein $R_3$ is $C_1$–$C_4$-alkylsulfonyl, phenylsulfonyl, $C_1$–$C_{12}$-alkylphenylsulfonyl or a group

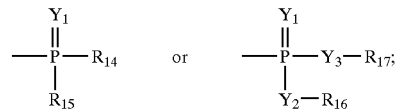

$R_6$, $R_7$, $R_8$ idependently of each other are hydrogen, $C_1$–$C_4$alkyl, or $R_{26}Y$—, or $R_6$ and $R_7$ together with the atoms to which they are bound form a 5- or 6-membered saturated or unsaturated ring which is unsubstituted or substituted by one or more $C_1$–$C_4$alkyl and which ring optionally is interrupted by one or more Y or to which ring other rings are condensed;

Q is $C_1$–$C_8$-alkylene optionally interrupted by one or more —O—;

X is —O— or —N $R_9$—;

$R_9$ is $C_1$–$C_6$alkyl, optionally interrupted by one or more —O—;

$R_{26}$ is $C_1$–$C_4$alkyl;

$Y_1$ and $Y_2$ are O;

$R_{14}$ and $R_{15}$ independently of one another are phenyl or methylphenyl;

$R_{16}$ and $R_{17}$ independently of one another are $C_1$–$C_4$-alkyl;

with the proviso that if $R_3$ is $CH_3C_6H_4SO_2$—, $R_6$, $R_7$ and $R_8$ are hydrogen and X is O, then $R_9$ is not methyl or ethyl.

Interesting are further compounds of formula V and VI, wherein $R_3$ is $C_1$–$C_4$-alkylsulfonyl, phenylsulfonyl, or $C_1$–$C_{12}$-alkylphenylsulfonyl;

$R_6$, $R_7$, $R_8$ independently of one another are hydrogen, $C_1$–$C_4$ alkyl, $R_{26}Y$— or phenyl, or $R_6$ and $R_7$ together with the atoms to which they are bound form a 5- or 6-membered saturated or unsaturated ring which optionally is substituted by one or more $C_1$–$C_4$alkyl and which ring is optionally interrupted by Y or to which ring other rings are condensed;

Q is $C_1$–$C_8$-alkylene optionally interrupted by one or more —O—;

X is —O—;

$R_9$ is $C_1$–$C_6$alkyl-, optionally interrupted by one or more —O—;

$R_{26}$ is $C_1$–$C_4$ alkyl;

with the proviso that, if $R_3$ is $CH_3C_6H_4SO_2$—, $R_6$, $R_7$ and $R_8$ are hydrogen and X is oxygen then $R_9$ is not methyl or ethyl.

Other interesting compounds of formulae V and VI are such, wherein $R_3$ is $C_1$–$C_4$-alkylsulfonyl, phenylsulfonyl, or $C_1$–$C_{12}$-alkylphenylsulfonyl;

$R_6$, $R_7$, $R_8$ independently of one another are hydrogen, $C_1$–$C_4$ alkyl, or $R_{26}Y$—;

X is —$NR_9$—; and $R_9$ is $C_1$–$C_6$alkyl-, optionally interrupted by one or more —O—.

Further interesting are compounds of formulae V and VI, wherein $R_3$ is a group $$\begin{array}{ccc} \overset{Y_1}{\underset{R_{15}}{\overset{\|}{-P}}}-R_{14}, & \overset{Y_1}{\underset{Y_2-R_{16}}{\overset{\|}{-P}}}-R_{14}, & \text{or} \quad \overset{Y_1}{\underset{Y_2-R_{16}}{\overset{\|}{-P}}}-Y_3-R_{17}; \end{array}$$

$R_6$, $R_7$, $R_8$ independently of one another are hydrogen, $R_{26}Y$—, $C_1$–$C_8$ alkyl optionally substituted by OH, $OR_{25}$, or $COOR_{25}$, or optionally interrupted by one or more —O—, or $R_6$ and $R_7$ together with the atoms to which they are bound form a 5- or 6-membered saturated or unsaturated ring which is unsubstituted or substituted by one or more $C_1$–$C_4$alkyl, or to which ring other rings are condensed;

Y is —O— or —S—;

X is —O— or —$NR_9$—;

$R_9$ is phenyl, $C_1$–$C_{12}$alkyl, optionally substituted by OH, or $OR_{25}$, or optionally interrupted by one or more —O—;

$R_{25}$ is $C_1$–$C_8$ alkyl which is unsubstituted or substituted by OH, O—$C_1$–$C_4$-alkyl or interrupted by one or more —O—:

$R_{26}$ is phenyl, $C_1$–$C_8$ alkyl optionally substituted by OH, $OR_{25}$, or $COOR_{25}$, or optionally interrupted by one or more —O—.

Other interesting compounds of formulae V and VI are compounds, wherein $R_3$ is a group $$\begin{array}{cc} \overset{Y_1}{\underset{R_{15}}{\overset{\|}{-P}}}-R_{14}, & \text{or} \quad \overset{Y_1}{\underset{Y_2-R_{16}}{\overset{\|}{-P}}}-Y_3-R_{17}; \end{array}$$

$R_6$, $R_7$, $R_8$ independently of one another are hydrogen, $C_1$–$C_4$ alkyl, or $R_{26}Y$—;

X, $Y_1$ and $Y_2$ are —O—;

x is 1;

$R_9$ is $C_1$–$C_6$alkyl, optionally interrupted by one or more —O—;

$R_{26}$ is $C_1$–$C_4$ alkyl;

$R_{14}$ and $R_{15}$ independently of each other are phenyl or methylphenyl; and $R_{16}$ and $R_{17}$ independently of each other are $C_1$–$C_4$-alkyl.

Most preferred are the compounds methyl α-(methylsulfonyloxyimino)-2-phenylacetate, propyl α-(4-methylphenylsulfonyloxyimino)-2-phenylacetate, methylethyl α-(4-methylphenylsulfonyloxyimino)-2-phenylacetate, butyl α-(4-methylphenylsulfonyloxyimino)-2-phenylacetate, hexyl α-(4-methylphenyl-sulfonyloxymino)-2-phenylacetate, 2-methoxyethyl α-(4-methylphenylsulfonyloxyimino)-2-phenylacetate, ethyl α-(4-methylphenylsulfonyloxyimino)-2-(4-methylphenyl)acetate, propyl α-(4-methylphenylsulfonyloxyimino)-2-(4-methylphenyl)acetate, butyl α-(4-methylphenyl-sulfonyloxyimino)-2-(4-methylphenyl)acetate, 2-methoxyethyl α-(4-methylphenylsulfonyloxyimino)-2-(4-methylphenyl)acetate, ethyl α-(4-methylphenyl-sulfonyloxyimino)-2-(4-ethylphenyl)acetate, ethyl α-(4-butylphenylsulfonyloxyimino)-2-(4-methylphenyl)acetate, ethyl α-(4-methylphenylsulfonyloxyimino)-2-(4-fluorophenyl)acetate, ethyl α-(4-methylphenyl-sulfonyloxyimino)-2-(4-methoxyphenyl)acetate, ethyl α-(4-methylphenylsulfonyloxyimino)-2-(3,4-dimethoxyphenyl)acetate, 2-methoxyethyl α-(4-methylphenyl-sulfonyloxyimino)-2-(3,4-dimethoxyphenyl)acetate, 2-methoxyethyl α-(methylsulfonyloxyimino)-2-(3,4-dimethoxyphenyl)acetate, methyl α-(4-methylphenyl-sulfonyloxyimino)-2-(4-methylthiophenyl)acetate, methyl α-(methylsulfonyloxyimino)-2-(4-methylthiophenyl)acetate, ethyl α-(4-methylphenylsulfonyloxyimino)-2-(4-methylthiophenyl)acetate, 2-methoxyethyl α-(4-methylphenylsulfonyloxyimino)-2-( 4-methylthiophenyl)acetate, 2-methoxyethyl α-(methylsulfonyloxyimino)-2-(4-methylthiophenyl)acetate, ethyl α-(4-methylphenyl-sulfonyloxyimino)-2-(3,4-butylthiophenyl)acetate, ethyl α-(4-methylphenylsulfonyloxyimino)-2-(4-dimethylaminophenyl)acetate, ethyl α-(4-methylphenylsulfonyloxyimino)-2-(thianthren-2-yl)acetate, methylsulfonyloxyimino-3,4-dimethoxyphenyl acetic acid 2-[2-(methylsulfonyloxyimino-3,4-dimethoxyphenyl-acetoxy)-ethoxy]-ethyl ester; N,N-diethyl α-(4-methylphenylsulfonyloxyimino)-2-phenylacetylamide, N,N-diethyl α-(methylsulfonyloxyimino)-2-phenylacetylamide, N,N-dibutyl α-(4-methylphenyl-sulfonyloxyimino)-2-phenylacetylamide, N,N-diethyl α-(4-methylphenylsulfonyloxyimino)-2-(4-ethylphenyl)acetylamide, methyl α-(diethoxyphosphoryloxyimino)-2-phenylacetate, ethyl α-(diethoxyphosphoryloxyimino)-2-phenylacetate, propyl α-(diethoxyphosphoryloxyimino)-2-phenylacetate; 2-methoxyethyl α-(diethoxyphosphoryl-oxyimino)-2-(3,4-dimethoxyphenyl)acetate, methyl α-(diethoxyphosphoryloxyimino)-2-(4-methylthiophenyl)acetate, ethyl α-(diethoxyphosphoryloxyimino)-2-(4-methylthiophenyl)acetate.

The invention also relates to mixtures of isomeric forms of the compounds of formula I, II, III, IV, V and VI. The double bond of the oxime group can exist in both the syn (cis, Z) and the anti (trans, E) form or as mixtures of the two geometrical isomers. In addition, the n double bonds of formulae I and II can, depending on the substituents $R_4$ and $R_5$, exhibit two (Z and E)) configurations. The substituted methylidene group $C(R_1)R_2$ of formula III and IV can also exhibit two (cis and trans) isomers. Depending on $R_4$, $R_5$ and A, this can result in up to four geometrical isomers. In the present invention, both the individual geometrical isomers and any mixtures of two or more geometrical isomers can be used.

Oxime derivatives (of formulae of formula I, II, III, IV, V and VI) can be prepared by methods described in the literature, for example by reacting suitable free oximes ($R_3$=H) with the desired (for example, sulfonic) acid halides (for example, $R_3Cl$ or $Cl$—$R_3$—$Cl$).

as described for example in Organic Syntheses coll. Vol. VI (J. Wiley & Sons, New York, 1988), pp 199 and 840, and acidic conditions, as described, for example, in Organic Synthesis coll. Vol V, pp 32 and 373, coll. Vol. III, pp 191 and 513, coil. Vol.II, pp. 202, 204 and 363, are suitable for the preparation of the oximes used as starting materials in the invention. Nitrous acid is usually generated from sodium nitrite. The alkyl nitrite can be for example methyl nitrite,

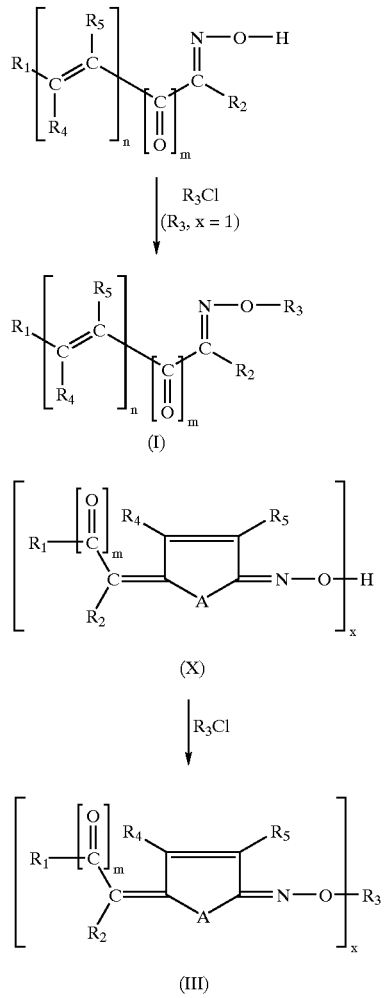

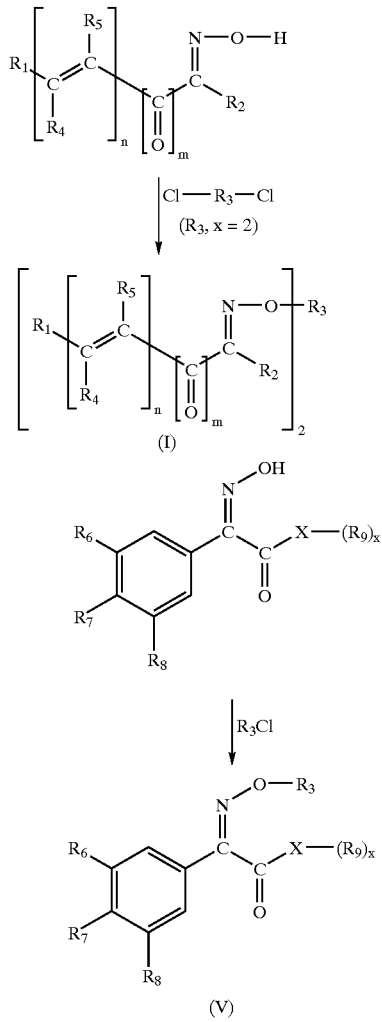

$R_1$, $R_2$, $R_3$, $R_4$, $R_5$, $R_6$, $R_7$, $R_8$, $R_9$, X, x, n and m are defined as described above.

These reactions are carried out in an inert solvent such as toluene, tetrahydrofuran (THF) or dimethylformamide (DMF) in the presence of a base, for example a tertiary amine, such as triethylamine, or by reaction of the salt of an oxime with the desired acid chloride. These methods are disclosed, for example, in EP 48615. The sodium salts of oximes can be obtained, for example, by reacting the oxime in question with a sodium alcoholate in dimethylformamide.

The compounds of formulae II, IV and VI are prepared in an analogous manner by starting with the corresponding dimeric hydroxyimino compounds.

The starting oximes ($R_3$=H) can be prepared in numerous ways, which are known to the person skilled in the art, for example by the nitrosation of "active" methylene groups with nitrous acid or an alkyl nitrite. Both alkaline conditions, ethyl nitrite, isopropyl nitrite, butyl nitrite, isoamyl nitrite. Another example is the oximation of cinnamaldehydes (Synthesis 1994, 573) followed by cyanation (J. Org. Chem. 1993, 58, 2075).

The oximes of formula X required for the reaction can be prepared according to known procedures, for example by reacting benzyl cyanides or cyanomethyl heterocycles with nitrobenzenes or nitronaphtalenes in the presence of a base (such as, for example, sodium methoxide or potassium hydroxide) in a polar solvent such as, for example, methanol or DMF, as described by R. B. Davis, L. C. Pizzini & E. J. Bara, J. Org. Chem. 26, 4270 (1961) or P. Fournary and T. Marey, Bull. Soc. Chim. Fr. 3223 (1968). Temperatures of −80° C. to 80° C., especially −10° C. to 60° C. are suitable for the reaction. Phase transfer catalysis is also suitable to prepare oxime intermediates of formula X. K.Takahashi, et al. have described the use of benzyltriethyl ammonium chloride and 50% aqueous sodium hydroxide for the reaction of nitrobenzene with benzyl cyanide (K. Takahashi, T. Tsuboi, K. Yamada, H. Iida, Nippon Kagaku Kaishi 144–7 (1976); Chemical Abstract No. 84:105162). Oximes of formula X have also been prepared as intermediates in the synthesis of various pharmaceutical compounds (e.g. U.S. Pat. Nos. 5,043,327, 5,521,187, EP 371564, EP541153, ES 524551) or for use as UV absorbers (for instance, in U.S. Pat. No. 3,374,248).

Oximes can also be obtained by reacting a suitable carbonyl or thionylcarbonyl compounds with hydroxylamine or a hydroxylammonium salt.

The preparation of the chlorides used to introduce the radical $R_3$ is known to the person skilled in the art. Many of these compounds are commercially available.

Another process for the preparation of the compounds according to the invention consists in that a ketone or an α-keto ester is brought into reaction with a solution of hydroxylamine or preferably a solution of the hydroxylamine hydrochloride salt thereof. Thus, α-(hydroxyimino)-2-phenylacetic acid ester can be conveniently prepared by the reaction of the corresponding α-keto phenylacetic acid ester with hydroxylamine or hydroxylamine hydrochloride in the presence of a base such as a tertiary amine or pyridine:

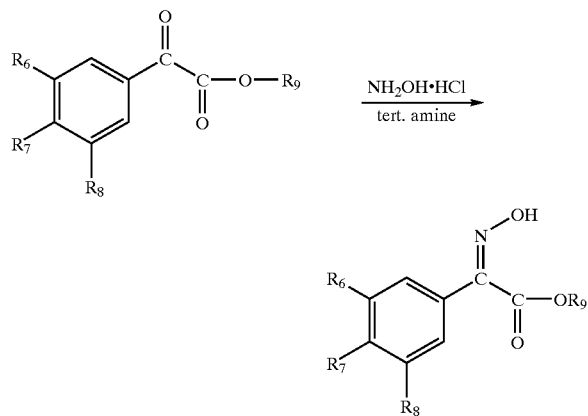

$R_6, R_7, R_8$ and $R_9$ have the meaning indicated above.

If requested, a solvent, such as for example diethyl ether, tert-butyl-methy-ether, dichloromethane or tetrahydrofuran, can be used. When the corresponding amides are used as starting materials, α-(hydroxyimino)-2-phenylacetic acid amides are obtained by the same procedure.

The composition according to the invention may additionally to the components (a), (b) and (c) comprise a binder polymer (d), and/or at least one further photoinitiator (e), and/or other additives (f) customary in the art.

The unsaturated compounds (a) may include one or more olefinic double bonds. They may be of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vi-nylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl) isocyanurate.

Examples of polyunsaturated compounds of relatively high molecular mass (oligomers) are acrylisized epoxy resins, acrylisized polyesters, polyesters containing vinyl ether or epoxy groups, and also polyurethanes and polyethers. Further examples of unsaturated oligomers are unsaturated polyester resins, which are usually prepared from maleic acid, phthalic acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, polybutadiene and butadiene copolymers, polyisoprene and isoprene copolymers, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acids are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the above-mentioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or completely esterified with one carboxylic acid or with different unsaturated carboxylic acids, and in partial esters the free hydroxyl groups may be modified, for example etherified or esterified with other carboxylic acids.

Examples of esters are:
  trimethylolpropane triacrylate, trimethylolethane triacrylate, trimethylolpropane trimeth-acrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripen-taerythritol octamethacrylate, pentaerythritol diitaconate, dipentaerythritol tris-itaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components (a) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriamine- trismethacrylamide, bis (methacrylamidopropoxy)ethane, β-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polybutadiene and polyisoprene and copolymers thereof are known. Examples of suitable comonomers are olefins, such as ethylene, propene, butene and hexene, (meth) acrylates, acrylonitrile, styrene or vinyl chloride. Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth) acrylic acid, or may be homo- and copolymers of (meth) acrylates which are esterified with hydroxyalkyl (meth) acrylates.

The photopolymerizable compounds can be used alone or in any desired mixtures. It is preferred to use mixtures of polyol (meth)acrylates.

Examples of the component (a) are also polymers or oligomers having at least two ethylenically unsaturated groups and at least one carboxyl function within the molecule structure, such as acid modified epoxyacrylates (for example, EB9696, UCB Chemicals; KAYARAD TCR1025, Nippon Kayaku Co.,LTD.), or acrylated acrylcopolymers (for example, ACA200M, Daicel Industries, Ltd.).

As component (a), a mono- or multi-functional ethylenically unsaturated compound, or mixtures of said compounds, can be included in the above composition up to 98% by weight based on the solid portion of the composition.

The unsaturated compounds (a) can also be used as a mixture with non-photopolymerizable, film-forming components. These may, for example, be physically drying polymers or solutions thereof in organic solvents, for instance nitrocellulose or cellulose acetobutyrate. They may also, however, be chemically and/or thermally curable (heat-curable) resins, examples being polyisocyanates, polyepoxides and melamine resins, as well as polyimide precursors. The use of heat-curable resins at the same time is important for use in systems known as hybrid systems, which in a first stage are photopolymerized and in a second stage are crosslinked by means of thermal postcure.

In the compositions according to the invention acrylate systems are especially preferred.

As examples of the coinitiator component (c), these are, in particular, aromatic compounds, for example benzophenone and derivatives thereof, thioxanthone and derivatives thereof, anthraquinone and derivatives thereof, coumarin and phenothiazine and derivatives thereof, and also 3-(aroylmethylene)thiazolines, rhodanine, camphorquinone, but also eosine, rhodamine, erythrosine, xanthene, thioxanthene, acridine, e.g. 9-phenylacridine, 1,7-bis(9-acridinyl)heptane, 1,5-bis(9-acridinyl)pentane, cyanine and merocyanine dyes. Specific examples coinitiators suitable as component (c) in the compositions according to the invention are 1. Thioxanthones Thioxanthone, 2-isopropylthioxanthone, 2-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbon-yl-3-chlorothioxanthone, 1-ethoxycarbonyl-3-ethoxy-thioxanthone, 1-ethoxycarbonyl-3-amino-thioxanthone, 1-ethoxycarbonyl-3-phenylsulfurylthioxanthone, 3,4-di-[2-(2-methoxyethoxy)-ethoxycarbonyl]-thioxanthone, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-carboxylic acid polyethyleneglycol ester, 2-hydroxy-3-(3,4-dimethyl-9-oxo-9H-thioxanthon-2-yloxy)-N,N,N-trimethyl-1-propanaminium chloride;

2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)-benzophenone, 4,4'-bis(diethylamino) benzophenone, 4-methyl benzophenone, 2,4,6-trimethylbenzophenone, 4-(4-methylthiophenyl)-benzophenone, 3,3'-dimethyl-4-methoxy benzophenone, methyl-2-benzoylbenzoate, 4-(2-hydroxyethylthio)-benzophenone, 4-(4-tolylthio)-benzophenone, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl)-benzophenone, 4-benzoyl-N,N-dimethyl-N-[2-(1-oxo-2-propen-yl)oxy]ethyl-benzenemethan-aminium chloride;

3. Coumarins

Coumarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)-coumarin], 3,3'-carbonyl-bis(7-methoxycoumarin), 3,3'-carbonyl-bis(7-diethylamino-coumarin), 3-isobutyroylcoumarin, 3-benzoyl-5,7-dimethoxy-coumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, 7-diethylamino-3-phenylcoumarin, the coumarin derivatives disclosed in JP 09-179299A and JP 09-325209A, for example 7-[{4-chloro-6-(diethylamino)-S-triazine-2-yl}amino]-3-phenylcoumarin;

4. 3-(aroylmethylene)-thiazolines 3-methyl-2-benzoylmethylene-β-naphthothiazoline, 3-methyl-2-benzoylmethylene-benzothiazoline, 3-ethyl-2-propionylmethylene-β-naphthothiazoline;

5. Rhodanines 4-dimethylaminobenzalrhodanine, 4-diethylaminobenzalrhodanine, 3-ethyl-5-(3-octyl-2-benzothiazolinylidene)-rhodanine, the rhodanine derivatives, formulae [1], [2], [7], disclosed in JP 08-305019A;

6. Other Compounds acetophenone, 3-methoxyacetophenone, 4-phenylacetophenone, benzil, 4,4'-bis(dimethylamino) benzil, 2-acetylnaphthalene, 2-naphthaldehyde, dansyl acid derivatives, 9,10-anthraquinone, anthracene, pyrene, aminopyrene, perylene, phenanthrene, phenanthrenequinone, 9-fluorenone, dibenzosuberone, curcumin, xanthone, thiomichler's ketone, α-(4-dimethylaminobenzylidene) ketones, e.g. 2,5-bis(4-diethylaminobenzylidene)cyclopentanone, 2-(4-dimethylamino-benzylidene)-indan-1-one, 3-(4-dimethylamino-phenyl)-1-indan-5-yl-propenone, 3-phenylthiophthalimide, N-methyl-3,5-di(ethylthio)-phthalimide, N-methyl-3,5-di(ethylthio)-phthalimide, phenothiazine, methylphenothiazine, amines, e.g. N-phenylglycine, ethyl 4-di-methylaminobenzoate, butoxyethyl 4-dimethylaminobenzoate, 4-dimethylamino-acetophenone, triethanolamine, methyldiethanolamine, dimethylaminoethanol, 2-(dimethylamino)ethyl benzoate.

A photopolymerizable composition, comprising as coinitiator (c) a compound selected from the group consisting of benzophenone derivatives, thioxanthone derivatives or coumarin derivatives is preferred.

The photopolymerizable compositions generally contain 0.005 to 20% by weight, for example 0.05 to 20% by weight, preferably 0.01 to 10% by weight, in particular 0.1 to 10% by weight, of the coinitiator, based on the solid composition.

Interesting is a photopolymerizable composition, comprising additionally at least one binder polymer (d).

As component (d), binders as well can be added to the novel compositions. This is particularly expedient when the photopolymerizable compounds are liquid or viscous substances. The quantity of binder may, for example, be 2–98%, preferably 5–95% and especially 20–90%, by weight relative to the overall solids content. The choice of binder is made depending on the field of application and on properties required for this field, such as the capacity for development in aqueous and organic solvent systems, adhesion to substrates and sensitivity to oxygen.

Examples of suitable binders are polymers having a molecular weight of about 2000 to 2000000, preferably 5000 to 1000000. Examples of alkali developable binders are acrylic polymer having carboxylic acid function as a pendant group, such as conventionally known copolymers obtained by copolymerizing an ethylenic unsaturated carboxylic acid such as (meth)acrylic acid, 2-carboxyethyl (meth)acrylic acid, 2-carboxypropyl (meth)acrylic acid ithaconic acid, crotonic acid, maleic acid and fumaric acid, with one or more monomers selected from esters of (meth)acrylic acid, such as methyl (meth)acrylate, ethyl (meth)acrylate, propyl (meth)acrylate, butyl (meth)acrylate, benzyl (meth)acrylate, 2-ethylhexyl (meth)acrylate, hydroxyethyl (meth)acrylate, hydroxypropyl (meth)acrylate, benzyl (meth)acrylate; vinyl aromatic compounds, such as styrene, α-methylstyrene, hydroxystyrene, vinyltoluene, p-chlorostyrene; amide type unsaturated compounds, (meth)acrylamide diacetonacrylamide, N-methylolacrylamide, N-butoxymethacrylamide; and polyolefin type compounds, such as butadiene, isoprene, chloroprene and the like; methacrylonitrile, methyl isopropenyl ketone, vinyl acetate, vinyl propionate, or vinyl pivalate. Preferable examples of copolymers are copolymers of methyl methacrylate/methacrylic acid, copolymers of benzyl methacrylate/methacrylic acid, copolymers of methyl methacrylate/-ethyl acrylate/methacrylic acid, copolymers of benzyl methacrylate/methacylic acid/styrene, copolymers of benzyl methacrylate/methacrylic acid/hydroxyethyl methacrylate, copolymers of methyl methacrylate/butyl methacrylate/methacrylic acid/styrene, copolymers of methyl methacrylate/benzyl methacrylate/methacrylic acid/hydroxyphenyl methacrylate. Examples of solvent developable binder polymers are poly(alkyl methacrylates), poly(alkyl acrylates); cellulose esters and cellulose ethers, such as cellulose acetate, cellulose acetobutyrate, methylcellulose, ethylcellulose; polyvinylbutyral, polyvinylformal, cyclized rubber, polyethers such as polyethylene oxide, polypropylene oxide and polytetrahydrofuran; polystyrene, polycarbonate, polyurethane, chlorinated polyolefins, polyvinyl chloride, vinyl chloride/vinylidene copolymers, copolymers of vinylidene chloride with acrylonitrile, methyl methacrylate and vinyl acetate, polyvinyl acetate, copoly(ethylene/vinyl acetate), polymers such as polycaprolactam and poly(hexamethylenadipamide), and polyesters such as poly(ethylene glycol terephtalate) and poly(hexamethylene glycol succinate) and polyimides.

Preferred is a photopolymerizable composition, comprising as binder polymer (d), a copolymer of methacrylate and methacrylic acid.

In addition to the photoinitiator (b) and coinitiator (c) the photopolymerizable mixtures may include various additives (f), which are customary in the art and the choice of which depends on the intended end use of the composition. Examples of these are thermal inhibitors, which are intended to prevent premature polymerization, examples being hydroquinone, hydroquinone derivatives, p-methoxyphenol, β-naphthol or sterically hindered phenols, such as 2,6-ditert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilizers are
1. 2-(2'-hydroxyphenyl)benzotriazoles for example 2-(2'-hydroxy-5'-methylphenyl)benzotriazole, 2-(3',5'-di-tert-butyl-2'-hydroxyphenyl)benzotriazole, 2-(5'-tert-butyl-2'-hydro-xyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methyl-phenyl)-5-chlorobenzotriazole, 2-(3'-sec-butyl-5'-tert-butyl-2'-hydroxyphenyl) benzotriazole, 2-(2'-hydroxy-4'-octoxyphenyl) benzotriazole, 2-(3', 5'-di-tert-amyl-2'-hydroxphenyl) benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethyl-hexyloxy)carbonylethyl]-2'-hydroxyphenyl)-5-chloro-benzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)-benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonyl-ethyl]-2'-hydroxyphenyl)benzotriazole, 2-(3'-dodecyl-2'-hydroxy-5'-methylphenyl)-benzotriazole, and 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]-benzotriazole with polyethylene glycol 300; [R—CH$_2$CH$_2$—COO(CH$_2$)$_3$]$_2$— where R=3'-tert-butyl-4'-hydroxy-5'-2H-benzotriazol-2-yl-phenyl.

2. 2-Hydroxybenzophenones, for example the 4-hydroxy-, 4-methoxy-, 4-octoxy-, 4-decyloxy-, 4-dodecyloxy-, 4-benzyloxy-, 4,2',4'-trihydroxy- and 2'-hydroxy-4,4'-dimethoxy derivative.

3. Esters of substituted or unsubstituted benzoicacids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbomethoxycinnamate, butyl or methyl α-cyano-β-methyl-p-methoxycinnamate, methyl α-carboxymethoxy-p-methoxycinnamate and N-(β-carbomethoxy-β-cyanovinyl)-2-methylindoline.

5. Sterically hindered amines, for example bis-(2,2,6,6-tetramethylpiperidyl) sebacate, bis-(2,2,6,6-tetramethylpiperidyl) succinate, bis-(1,2,2,6,6-pentamethylpiperidyl) sebacate, bis-(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6,6-tetramethyl-4-piperidyl)hexa-methylenediamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl)-1,2,3,4-butane tetraoate, 1,1'-(1,2-ethandiyl)bis(3,3,5,5-tetramethyl-piperazinone), 4-benzoyl-2,2,6,6-tetramethylpiperidine, 4-stearyloxy-2,2,6,6-tetramethylpiperidine, bis-(1,2,2,6,6-pentamethylpiperidyl) 2-n-butyl-2-(2-hydroxy-3,5-di-tert-butylbenzyl) malonate, 3-n-octyl-7,7,9,9-tetramethyl-1,3,8-triazaspiro-[4.5]decane-2,4-dione, bis-(1-octyloxy-2,2,6,6-tetramethylpiperidyl) sebacate, bis-(1-octyloxy-2,2,6,6-tetramethylpiperidyl) succinate, condensation product of N,N'-bis-(2,2,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis-(3-aminopropyl-amino)ethane, condensation product of 2-chloro-4,6-di-(4-n-butylamino-1,2,2,6,6-pentamethylpiperidyl)-1,3,5-triazine and 1,2-bis-(3-aminopropylamino)-ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione and 3-dodecyl-1-(1,2,2,6,6-penta-methyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide, mixtures of o- and p-meth-oxy- and of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyl-oxy-phenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4- dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl/tridecyl-oxy-(2-hydroxypropyl)oxy-2-hydroxy-phenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, bis-(2,6-di-tert-butyl-4-methylphenyl) pentaerythrityl diphosphite, bis-isodecyloxy pentaerythrityl diphosphite, bis-(2,4-di-tert-butyl-6-methylphenyl) pentaerythrityl diphosphite, bis-(2,4,6-tri-tert-butylphenyl) pentaerythrityl diphosphite, tristearyl sorbityl triphosphite, tetrakis-(2,4-di-tertbutylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis-(2,4-di-tert-butyl-6-methylphenyl) methyl phosphite and bis(2,4-di-tert-butyl-6-methylphenyl) ethyl phosphite.

Further additives known in the art may be added as component (f), as for example flow improvers and adhesion promoters.

To accelerate the photopolymerization it is possible to add amines, for example triethanolamine, N-methyldiethanolamine. The action of the amines can be intensified by the addition of aromatic ketones. Examples of amines which can be used as oxygen scavengers are substituted N,N-dialkylanilines, as are described, for example, in EP 339841. Other accelerators and autoxidizers are thiols, thioethers, disulfides, phosphonium salts, phosphine oxides or phosphines, as described, for example, in EP 438123, GB 2180358 and JP Kokai Hei 6-68309.

It is further possible to add chain transfer agents which are customary in the art to the compositions according to the invention. Examples are mercaptans, amines and benzothiazol.

The curing process, in particular of compositions which are pigmented (for example with titanium dioxide), can be assisted by adding a component which under thermal conditions forms free radicals, for example an azo compound such as 2,2'-azobis(4-methoxy-2,4-dimethylvaleronitrile), a triazene, a diazo sulfide, a pentazadiene or a peroxy compound, for instance a hydroperoxide or peroxycarbonate, for example t-butyl hydroperoxide, as is described for example in EP 245639.

Further customary additives (f), depending on the intended use, are optical brighteners, fillers, pigments, dyes, wetting agents or levelling assistants. In order to cure thick and pigmented coatings it can be appropriate to add glass microspheres or pulverized glass fibres, as described for example in U.S. Pat. No. 5,013,768.

The choice of additive(s) (f) is made depending on the field of application and on properties required for this field. The additives described above are customary in the art and accordingly are added in amounts which are usual in the respective application.

In particular, further additives (f) are pigments which are added to the compositions according to the invention especially when these are used for the preparation of color filters. Examples of suitable pigments are given below.

In particular red, green, blue and black pigments are used as component (f).

The invention also provides compositions comprising as component (a) at least one ethylenically unsaturated photopolymerizable compound which is emulsified or dissolved in water. Many variants of such radiation-curable aqueous prepolymer dispersions are commercially available. A prepolymer dispersion is understood as being a dispersion of water and at least one prepolymer dispersed therein. The concentration of water in these systems is, for example, from 5 to 80% by weight, in particular from 30 to 60% by weight. The concentration of the radiation-curable prepolymer or prepolymer mixture is, for example, from 95 to 20% by weight, in particular from 70 to 40% by weight. In these compositions the sum of the percentages given for water and prepolymer is in each case 100, with auxiliaries and additives being added in varying quantities depending on the intended use. The radiation-curable, film-forming prepolymers which are dispersed in water and are often also dissolved are aqueous prepolymer dispersions of mono- or polyfunctional, ethylenically unsaturated prepolymers which are known per se, can be initiated by free radicals and have for example a content of from 0.01 to 1.0 mol of polymerizable double bonds per 100 g of prepolymer and an average molecular weight of, for example, at least 400, in particular from 500 to 10000. Prepolymers with higher molecular weights, however, may also be considered depending on the intended application. Use is made, for example, of polyesters containing polymerizable C—C double bonds and having an acid number of not more than 10, of polyethers containing polymerizable C—C double bonds, of hydroxyl-containing reaction products of a polyepoxide, containing at least two epoxide groups per molecule, with at least one α,β-ethylenically unsaturated carboxylic acid, of polyurethane (meth)acrylates and of acrylic copolymers which contain α,β-ethylenically unsaturated acrylic radicals, as are described in EP 12339. Mixtures of these prepolymers can likewise be used. Also suitable are the polymerizable prepolymers described in EP 33896, which are thioether adducts of polymerizable prepolymers having an average molecular weight of at least 600, a carboxyl group content of from 0.2 to 15% and a content of from 0.01 to 0.8 mol of polymerizable C—C double bonds per 100 g of prepolymer. Other suitable aqueous dispersions, based on specific alkyl (meth)acrylate polymers, are described for example in EP 41125, and suitable water-dispersible, radiation-curable prepolymers of urethane acrylates can be found in DE 2936039. Some suitable UV curable urethane acrylate dispersions are supplied for example by ZENECA, such as NeoRad NR-440 and NeoRad NR-3709. Further additives which may be included in the radiation-curable aqueous prepolymer dispersions are dispersion auxiliaries, emulsifiers, antioxidants, light stabilizers, dyes, pigments, fillers, for example talc, gypsum, silicic acid, rutile, carbon black, zinc oxide, iron oxides, reaction accelerators, levelling agents, lubricants, wetting agents, thickeners, flatting agents, antifoams and other auxiliaries customary in paint technology. Suitable dispersion auxiliaries are water-soluble organic compounds which are of high molecular mass and contain polar groups, examples being polyvinyl alcohols, polyvinylpyrrolidone or cellulose ethers. Emulsifiers which can be used are nonionic emulsifiers and, if desired, ionic emulsifiers as well. Such additives are added in customary amounts, known to the person skilled in the art, and depending of the intended use of the composition.

In certain cases it may be of advantage to use mixtures of two or more of the said photoinitiators (b). It is of course also possible to use mixtures with other known radical photoinitiators (e), for example mixtures with α-hydroxycyclohexyl phenyl ketone, 2-hydroxy-2-methyl- 1-phenyl-propanone, (α-hydroxy- or α-aminoacetophenones, e.g. (4-methylthiobenzoyl)-1-methyl-1-morpholinoethane, (4-morpholinobenzoyl)-1-benzyl-1-dimethylaminopropane, 4-aroyl-1,3-dioxolanes, benzoin alkyl ethers, dim ethyl benzil ketal, phenylglyoxalic esters and derivatives thereof, dimeric phenylglyoxalic esters, peresters, e,g. benzophenone tetracarboxylic peresters as described for example in EP 126541, monoacyl phosphine oxides, e.g. (2,4,6-trimethylbenzoyl)diphenylphosphine oxide, bisacylphosphine oxides, e.g. bis(2,6-di-methoxybenzoyl)-(2,4,4-trimethyl-pentyl)phosphine oxide, bis(2,4,6-trimethylbenzoyl)-phenylphosphine oxide, bis(2,4,6-trimethylbenzoyl)-2,4-dipentoxyphenylphosphine oxide, trisacylphosphine oxides, trihalomethyltriazines, e.g. 2-[2-(4-methoxyphenyl)vinyl]-4,6-bis(trichloromethyl)-1,3,5-triazine, 2-(4-methoxyphenyl)-4,6-bis(trichloromethyl)-1,3,5-triazine, 2-(3,4-dimethoxyphenyl)-4,6-bis(trichloromethyl)-1,3,5-triazine, 2-methyl-4,6-bis(trichloromethyl)-1,3,-5-triazine, 2-[p-N,N-di(ethoxycarbonylmethyl)aminophenyl]-4,6-bis(trichloromethyl)-1,3,5-triazine, 2-(4-methoxynaphthyl)-4,6-bis(trichloromethyl)-1,3,5-triazine, 2-(1,3-benzodioxol-5-yl)-4,6-bis(trichloromethyl)-1,3,5-triazine, 2-[2-(4-pentyloxyphenyl)vinyl]-4,6-bis(trichloromethyl)-1,3,5-triazine, 2-[2-(3-methylfuran-2-yl)vinyl]-4,6-bis(trichloromethyl)-1,3,5-triazine, 2-methylfuran-2-yl)vinyl]-4,6-bis(trichloromethyl)-1,3,5-triazine, 2-[2-(2,4-dimethoxyphenyl)vinyl]-4,6-bis(trichloromethyl)-1,3,5-triazine, 2-[2-(2-methoxyphenyl)vinyl]-4,6-bis(trichloromethyl)-1,3,5-triazine, 2-[2-(4-isopropyloxyphenyl)vinyl]-4,6-bis(trichloromethyl)-1,3,5-triazine, 2-[2-(3-chloro-4methoxy-phenyl)vinyl]-4,6-bis(trichloromethyl)-1,3,5-triazine, 2-[2-bromo-4N,N-di(ethoxycarbopnylmethyl)aminophenyl]-4,6-bis(trichloromethyl)-1,3,5-triazine, 2-[2-chloro-4-N,N-di(ethoxycarbopnylmethyl)aminophenyl]-4,6-bis(trichloromethyl)-1,3,5-triazine, 2-[3-bromo-4-N,N-di(ethoxycarbopnylmethyl)aminophenyl]-4,6-bis(trichloromethyl)-1,3,5-triazine, 2-[3-chloro-4-N,N-di(ethoxycarbopnylmethyl)aminophenyl]-4,6-bis(trichloromethyl)-1,3,5-triazine; or other halomethyltriazines as described a) by G. Buhr, R. Dammel and C. Lindley in Polym. Mater. Sci. Eng. 61, 269 (1989), b) in EP 262788, furthermore halomethyl-oxazol photoinitiators, such as described in U.S. Pat. No. 4,371,606 and U.S. Pat. No. 4,371,607, 1,2-disulfones, such as described by E. A. Bartmann in Synthesis 5, 490 (1993); hexaarylbisimidazole/coinitiator systems, e.g. ortho-chlorohexaphenyl-bisimidazole combined with 2-mercaptobenzthiazole, borates, borate/coinitiator systems, O-acyloximes, e.g. benzophenoneoxime O-acetate, 4,4'-bis-(diethylamino)benzophenoneoxime O-acetate, 1-phenyl-1,2-propanedione-2-O-benzoyl oxime, oxime carbonates, e.g. 1-phenyl-1,2-propanedione-2-ethoxycarbonyl oxime, ferrocenium compounds, or titanocenes, e.g. bis(cyclopentadienyl)-bis(2,6-difluoro-3-pyrryl-phenyl)titanium.

Mention should be made of a photopolymerizable composition, comprising in addition to the photoinitiator (b) at least one further photoinitiator (e), and/or other additives (f), in particular pigments or dyes.

The photopolymerizable compositions generally contain 0.05 to 20% by weight, preferably 0.1 to 10% by weight, of the photoinitiator, based on the solid composition. The amount refers to the sum of all photoinitiators added, if mixtures of initiators are employed. Accordingly, the amount either refers to the photoinitiator (b) or the photoinitiators (b)+(e).

The photopolymerizable compositions can be used for various purposes, for example as printing ink, as a clear finish, as a white finish, for example for wood or metal, as powder coating, as a coating material, inter alia for paper, wood, metal or plastic, as a daylight-curable coating for the marking of buildings and road marking, for photographic reproduction techniques, for holographic recording materials, for image recording techniques or to produce printing plates which can be developed with organic solvents or with aqueous alkalis, for producing masks for screen printing, as dental filling compositions, as adhesives, as pressure-sensitive adhesives, as laminating resins, as etch resists, electroplating resists, or permanent resists, both liquid and dry films, as photopatternable dielectric layer or coating and as solder masks for electronic circuits, as photosensitive materials to produce spacers, protective films, prism sheets or sealing materials in liquid crystalline displays, as resists to manufacture color filters (color mosaic) for any type of display applications or to generate structures in the manufacturing process of plasma-display panels and electroluminescence displays, for the production of optical switches, optical lattices (interference lattice), light circuits, for producing three-dimensional articles by mass curing (UV curing in transparent moulds) or by the stereolithography technique, as is described, for example, in U.S. Pat. No. 4,575,330, to produce composite materials (for example styrenic polyesters, which may, if desired, contain glass fibres and/or other fibres and other auxiliaries) and other thick-layered compositions, for coating or sealing electronic components and chips, or as coatings for optical fibres, or for producing optical lenses, e.g. contact lenses or Fresnel lenses. The compositions according to the invention are further suitable for the production of medical equipment, auxiliaries or implants. Further the compositions according to the invention are suitable for the preparation of gels with thermotropic properties, as for example described in DE 19700064 and EP 678534.

The photoinitiators may additionally be employed as initiators for emulsion polymerizations, pearl polymerizations or suspension polymerizations, as polymerization initiators for fixing ordered states of liquid-crystalline monomers and oligomers, or as initiators for fixing dyes on organic materials.

In coating materials, use is frequently made of mixtures of a prepolymer with polyunsaturated monomers, which may additionally include a monounsaturated monomer as well. It is the prepolymer here which primarily dictates the properties of the coating film, and by varying it the skilled worker is able to influence the properties of the cured film. The polyunsaturated monomer functions as a crosslinking agent which renders the film insoluble. The monounsaturated monomer functions as a reactive diluent, which is used to reduce the viscosity without the need to employ a solvent. Unsaturated polyester resins are usually used in two-component systems together with a monounsaturated monomer, preferably with styrene. For photoresists, specific one-component systems are often used, for example polymaleimides, polychalcones or polyimides, as described in DE 2308830.

The photoinitiators and mixtures thereof can also be used for the polymerization of radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (for example methyl methylacrylamidoglycolate) and a novel free-radical photoinitiator, such formulations being as described, for example, in the paper "Radiation Curing of Powder Coating", Conference Proceedings, Radtech Europe 1993 by M. Wittig and Th. Gohmann. The powder coatings can also contain binders, as are described, for example, in DE 4228514 and in EP 636669. Free-radically UV-curable powder coatings can also be formulated by mixing unsaturated polyester resins with solid acrylates, methacrylates or vinyl ethers and with a novel photoinitiator (or photoinitiator mixture). The powder coatings may also comprise binders as are described, for example, in DE 4228514 and in EP 636669. The UV-curable powder coatings may additionally comprise white or coloured pigments. For example, preferably rutiletitanium dioxide can be employed in concentrations of up to 50% by weight in order to give a cured powder coating of good hiding power. The procedure normally comprises electrostatic or tribostatic spraying of the powder onto the substrate, for example metal or wood, melting of the powder by heating, and, after a smooth film has formed, radiation-curing of the coating with ultraviolet and/or visible light, using for example medium-pressure mercury lamps, metal halide lamps or xenon lamps. A particular advantage of the radiation-curable powder coatings over their heat-curable counterparts is that the flow time after melting the powder particles can be delayed in order to ensure the formation of a smooth, high-gloss coating. In contrast to heat-curable systems, radiation-curable powder coatings can be formulated to melt at lower temperatures without the unwanted effect of shortening their lifetime. For this reason, they are also suitable as coatings for heat-sensitive substrates, for example wood or plastics. In addition to the photoinitiator systems, the powder coating formulations may also include UV absorbers. Appropriate examples are listed above.

The novel photocurable compositions are suitable, for example, as coating materials for substrates of all kinds, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$ to which it is intended to apply a protective layer or, by means of imagewise exposure, to generate an image.

Coating of the substrates can be carried out by applying to the substrate a liquid composition, a solution or a suspension. The choice of solvents and the concentration depend principally on the type of composition and on the coating technique. The solvent should be inert, i.e. it should not undergo a chemical reaction with the components and should be able to be removed again, after coating, in the course of drying. Examples of suitable solvents are ketones, ethers and esters, such as methyl ethyl ketone, isobutyl methyl ketone, 2-pentanone, 2-hexanone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, ethoxyethyl acetate, n-butyl acetate, propylene glycol monomethyl ether acetate, diethylene glycol monoethyl ether acetate, ethyl lactate, methyl 3-methoxypropionate, methyl 3-ethoxypropionate, dipropylene glycol monomethyl ether and ethyl 3-ethoxypropionate. In certain cases it may be of advantage to use mixtures of two or more of the said solvents. The solution is applied uniformly to a substrate by means of known coating techniques, for example by spin coating, dip coating, knife coating, curtain coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination. The quantity applied (coat thickness) and the nature of the substrate (layer support) are dependent on the desired field of application. The range of coat thicknesses generally comprises values from about 0.05 $\mu$m to more than 100 $\mu$m, for example 0.05 $\mu$m to 1 cm, preferably 0.1 $\mu$m to 500 $\mu$m. The photocurable compositions according to the invention are especially suitable for the preparation of thin films.

The novel radiation-sensitive compositions further find application as negative resists, having a very high sensitivity to light and being able to be developed in an aqueous alkaline medium without swelling. They are suitable as photoresists for electronics like electroplating resist, etch resist, both liquid and dry films, solder resist, as resists to manufacture color filters for any type of display applications or to generate structures in the manufacturing process of plasma-display panels and electroluminescence displays, the production of printing plates, such as offset printing plates or screen printing plates, for the production of printing forms for relief printing, planographic printing, rotogravure or of screen printing forms, for the production of relief copies, for example for the production of texts in braille, for the production of stamps, for use in chemical milling or as a microresist in the production of integrated circuits. The compositions further may be used as photopatternable dielectric layer or coating, encapsulating material and isolating coating in the production of computer chips, printed boards and other electric or electronic components. The possible layer supports, and the processing conditions of the coating substrates, are just as varied.

Because the photocurable compositions according to the invention have a good thermal stability and are sufficiently resistant to inhibition by oxygen, they are particularly suitable for the production of color filter or color mosaic systems, such as described, for example, in EP 320 264. Color filter systems usually are employed in the manufacturing of LCD displays or image sensors. The color filter systems usually are prepared by forming red, green and blue pixels and a black matrix on a glass substrate. In these processes photocurable compositions according to the invention can be employed. A particularly preferred method of use comprises the coating of the substrate with the composition of the invention, drying of the coating with a short heat treatment, patternwise exposure of the coating to actinic radiation and subsequent development of the pattern in an aqueous alkaline developer solution and finally a heat treatment. Thus, by subsequently applying a red, green and blue pigmented coating on top of each other with this process a color filter layer can be produced. The color filter systems can be used, for example, for display and image scanner in television receivers, video monitors or computers, in flat panel display technology etc. In such color filter systems as the red pigment, for instance, an anthraquinone pigment, e.g. C. I. Pigment Red 177 ("C.I." refers to the Color Index, known to the person skilled in the art and publicly available), or a perylene pigment, e.g. C. I. Pigment Red 155, is used either alone or in the form of a mixture with a diazo yellow pigment or an isoindoline type yellow pigment. Especially advantageous is their mixture with C.I. Pigment Yellow 83 or C. I. Pigment Yellow 139 Further suitable examples for the pigment are such of C.I. Pigment Red 144, 177,185, 202, 209, 214, 222, 254, 255, 264, 272 and C.I. Pigment Yellow 83, 93, 95, 109, 110, 128, 129, 138, 139, 166. As green pigment, for example, halogenated phthalocyanine type pigments are used either alone or in combination with a diazo yellow pigment or an isoindoline type yellow pigment, for example, a combination of C.I. Pigment Green 7, 36, 136 or 37 and C. I. Pigment Yellow 83 or C.I. Pigment Yellow 139. Examples for suitable blue pigments are phthalocyanine type pigments, used either alone or in combination with an dioxazine type violet pigment, for instance, a combination of C. I. Pigment Blue 15:3 and C. I. Pigment Violet 23. Further examples for blue pigments are such of C.I. Blue 15:4, 15:6, 16 and 60. Other suitable pigments are such of C.I. Violet 19, 23, 32, 37,177 and C.I. Orange 73. Also combinations of two or three pigments are used. Especially suitable in color filter applications are powdery processed pigments prepared by finely dispersing the above mentioned pigments into a resin. Examples of pigments used in the black matrix are, carbon black, titanium black, iron oxide, C.I. Pigment Black 1 and 7, which are used either alone or in combination. The concentration of the pigment in the total solid component (pigments of various colors and resin) is for example in the range of 10% to 50% by weight, in particular in the range of 20% to 40% by weight.

The compositions according to the invention also find application for the production of one-or more-layered materials for the image recording or image reproduction (copies, reprography), which may be mono- or polychromatic. Furthermore the materials are suitable for color proofing systems. In this technology formulations containing microcapsules can be applied and for the image production the radiation curing can be followed by a thermal treatment. Such systems and technologies and their applications are for example disclosed in U.S. Pat. No. 5,376,459.

Substrates used for photographic information recordings include, for example, films of polyester, cellulose acetate or polymer-coated papers; substrates for offset printing formes are specially treated aluminium, substrates for producing printed circuits are copper-clad laminates, and substrates for producing integrated circuits are silicon wafers. The layer thicknesses for photographic materials and offset printing formes is generally from about 0.5 μm to 10 μm, while for printed circuits it is from 1.0 μm to about 100 μm. Following the coating of the substrates, the solvent is removed, generally by drying, to leave a coat of the photoresist on the substrate.

The term "imagewise" exposure includes both, exposure through a photomask comprising a predetermined pattern, for example a slide, as well as exposure by means of a laser or light beam, which for example is moved under computer control over the surface of the coated substrate and in this way produces an image, and irradiation with computer-controlled electron beams. It is also possible to use masks made of liquid crystals that can be adressed pixel by pixel to generate digital images, as is, for example, described by A. Bertsch, J. Y. Jezequel, J. C. Andre in Journal of Photochemistry and Photobiology A: Chemistry 1997, 107, p. 275–281 and by K.-P. Nicolay in Offset Printing 1997, 6, p. 34–37. Following the imagewise exposure of the material and prior to development, it may be advantageous to carry out thermal treatment for a short time. In this case only the exposed sections are thermally cured. The temperatures employed are generally 50–150° C., preferably 80–130° C.; the period of thermal treatment is in general between 0.25 and 10 minutes.

The photocurable composition may additionally be used in a process for producing printing plates or photoresists as is described, for example, in DE 4013358. In such a process the composition is exposed for a short time to visible light with a wavelength of at least 400 nm, without a mask, prior to, simultaneously with or following imagewise irradiation.

After the exposure and, if implemented, thermal treatment, the unexposed areas of the photosensitive coating are removed with a developer in a manner known per se.

As already mentioned, the novel compositions can be developed by aqueous alkalis. Particularly suitable aqueous-alkaline developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

Photocuring is of great importance for printings, since the drying time of the ink is a critical factor for the production rate of graphic products, and should be in the order of fractions of seconds. UV-curable inks are particularly important for screen printing and offset inks.

As already mentioned above, the novel mixtures are highly suitable also for producing printing plates. This application uses, for example, mixtures of soluble linear polyamides or styrene/butadiene and/or styrene/isoprene rubber, polyacrylates or polymethyl methacrylates containing carboxyl groups, polyvinyl alcohols or urethane acrylates with photopolymerizable monomers, for example acrylamides and/or methacrylamides, or acrylates and/or methacrylates, and a photoinitiator. Films and plates of these systems (wet or dry) are exposed over the negative (or positive) of the printed original, and the uncured parts are subsequently washed out using an appropriate solvent or aqueous solutions. Another field where photocuring is employed is the coating of metals, in the case, for example, of the coating of metal plates and tubes, cans or bottle caps, and the photocuring of polymer coatings, for example of floor or wall coverings based on PVC. Examples of the photocuring of paper coatings are the colourless varnishing of labels, record sleeves and book covers.

Also of interest is the use of the novel photoinitiators for curing shaped articles made from composite compositions. The composite compound consists of a self-supporting matrix material, for example a glass fibre fabric, or alternatively, for example, plant fibres [cf. K.-P. Mieck, T. Reussmann in Kunststoffe 85 (1995), 366–370], which is impregnated with the photocuring formulation. Shaped parts comprising composite compounds, when produced using the novel compounds, attain a high level of mechanical stability and resistance. The novel compounds can also be employed as photocuring agents in moulding, impregnating and coating compositions as are described, for example, in EP 7086. Examples of such compositions are gel coat resins, which are subject to stringent requirements regarding curing activity and yellowing resistance, and fibre-reinforced mouldings, for example, light diffusing panels which are planar or have lengthwise or crosswise corrugation. Techniques for producing such mouldings, such as hand lay-up, spray lay-up, centrifugal casting or filament winding, are described, for example, by P. H. Selden in "Glasfaserverstärkte Kunststoffe", page 610, Springer Verlag Berlin-Heidelberg-New York 1967. Examples of articles which can be produced by these techniques are boats, fibre board or chipboard panels with a double-sided coating of glass fibre-reinforced plastic, pipes, containers, etc. Further examples of moulding, impregnating and coating compositions are UP resin gel coats for mouldings containing glass fibres (GRP), such as corrugated sheets and paper laminates. Paper laminates may be based on urea resins or melamine resins. Prior to production of the laminate, the gel coat is produced on a support (for example a film). The novel photocurable compositions can also be used for casting resins or for embedding articles, for example electronic components, etc.

The compositions and compounds according to the invention can be used for the production of holographies, waveguides, optical switches wherein advantage is taken of the development of a difference in the index of refraction between irradiated and non-irradiated areas.

The use of photocurable compositions for imaging techniques and for the production of information carriers, electronic circuits, plating masks and micromechanical parts is also important. In such applications, as already described above, the layer (wet or dry) applied to the support is irradiated imagewise, e.g through a photomask, with UV or visible light, and the unexposed areas of the layer are removed by treatment with a developer. Application of the photocurable layer to metal can also be carried out by electrodeposition. The exposed areas are crosslinked and are therefore insoluble in the developer and remain on the support. Appropriate colouration produces visible images. Where the support is a metallized layer, the metal can, following exposure and development, be etched away at the unexposed areas or reinforced by electroplating.

The photosensitivity of the novel compositions can extend in general from about 190 nm to 600 nm. Suitable radiation is present, for example, in sunlight or light from artificial light sources. Consequently, a large number of different types of light sources are employed. Both, point sources and arrays ("lamp carpets") are suitable. Examples are carbon arc lamps, xenon arc lamps, medium-, high- and low-pressure mercury lamps, optionally metal halide doped (metal-halogen lamps), microwave-stimulated metal vapour lamps, excimer lamps, superactinic fluorescent tubes, fluorescent lamps, argon incandescent lamps, electronic flashlights, photographic flood lamps, light emitting diodes (LED), and excimer lasers. Electron beams and X-rays can also be used. The distance between the radiation source and the substrate to be exposed in accordance with the invention may vary depending on the intended application and the type and power density of the radiation source and the optical path, and may be, for example, from 1 cm to 150 cm. Laser light sources, for example excimer lasers, such as KrF lasers for exposure at 248 nm and ArF lasers at 193 nm are also suitable. Lasers in the visible region can also be employed, for example argon laser, frequency doubled YAG laser. By this method it is possible to produce integrated circuits and printed circuits in the electronics industry, lithographic offset printing plates or relief printing plates, and also photographic image recording materials.

The invention therefore also provides a process for the photopolymerization of monomeric, oligomeric or polymeric compounds containing at least one ethylenically unsaturated double bond, which comprises adding to the above mentioned compounds at least one photoinitiator of the formula I, II, III, IV, V or VI as described above and a coinitiator (c) and irradiating the resulting composition with electromagnetic radiation, in particular light of the wavelength 190 to 600 nm, with e-beam radiation or with X-rays.

The invention additionally provides compositions for producing pigmented and nonpigmented paints and varnishes, powder coatings, printing inks, printing plates, adhesives, dental compositions, resist materials, including photoresists, color filter materials, as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, and as image recording material, especially for holographic recordings, microelectronic circuits, decolorizing materials, decolorizing materials for image recording materials, for image recording materials using microcapsules; and a process for producing pigmented and non-pigmented paints and varnishes, powder coatings, printing inks, printing plates, adhesives, dental compositions, composite compositions, resists, including photoresists, color filter materials, compositions for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of microlithography, plating, stereolithography, for producing image recording materials, especially for holographic recordings, microelectronic circuits, decoloriozing materials, decolorizing materials for image recording materials, for image recording materials using microcapsules.

The invention further provides a coated substrate which is coated on at least one surface with a composition as described above, and further pertains to a process for the production of relief images, in which a coated substrate is subjected to imagewise exposure and then the unexposed portions are removed with a solvent. As "solvent" in this connection not only organic solvents are used, but also and in particular aqueous alkaline developers are employed. Imagewise exposure may be effected by irradiating through a mask or by means of a laser, X-ray or electron beam. Of particular advantage in this context is the laser beam exposure already mentioned above.

The compounds of the invention have a high sensitivity and resolution at low concentration with a coinitiator. They have a good thermal stability and low volatility.

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

A) PREPARATION EXAMPLES

Example 1

Preparation of 2-methoxyethyl α-(4-methylphenylsulfonyloxyimino)-2-phenylacetate 1.1 2-Methoxyethyl phenylglyoxalate In a flask equipped with a distillation apparatus, 164.2 g (1 mol) of methyl phenylglyoxalate and 49.8 g (0.2 mol) of dibutyltin oxide are added to 400 ml of 2-methoxyethanol and heated to reflux for 16 hours. Methanol is distilled off during this time. Excess 2-methoxy ethanol is subsequently distilled in vacuo to give a crude reaction product which is purified by filtration over silica gel. After evaporation of the solvent, 208 g (100%) of 2-methoxyethyl phenylglyoxalate are obtained as a colorless liquid.

$^1$H-NMR (CDCl$_3$), δ[ppm]: 8.00 (m, 2 aromatic H); 7.63 (m, 1 aromatic H); 7,50 (m, 2 aromatic H); 4.51 (dxd; 2H, COOCH$_2$—); 3.69 (dxd, 2H, —CH$_2$—O—); 3.39 (s, 3H, CH$_3$O).

1.2 2-Methoxyethyl α-(hydroxyimino)-2-phenylacetate 61.7 g (0.296 mol) of 2-methoxyethyl phenylglyoxalate are dissolved in 360 ml pyridine. 22.7 g (0.0.326 mol) of hydroxylammonium hydrochloride are added in portions to this solution. When the addition is complete, the reaction mixture is stirred at room temperature for 2 hours. After addition of ethyl acetate and water, the organic layer is separated, washed with diluted HCl and water and dried over magnesium sulfate. Evaporation of the solvent gives 68 g (100%) of crude 2-methoxyethyl α-(hydroxyimino)-2- phenylacetate as a slightly brownish liquid. This compound is used without further purification in the next step.

¹H-NMR (CDCl₃), δ [ppm]: 7.60–7.25 (m, 5 aromatic H); 4.54 and 4.43 (dxd, 2H, trans and cis COOCH₂—); 3.70 and 3.65 (dxd, 2H, trans and cis —CH₂—O—); 3.39 (s, 3H, CH₃O). The trans/cis isomer ratio is approximately 3:1.

1.3 2-Methoxyethyl α-(4-methylphenylsulfonyloxyimino)-2-phenylacetate

A solution of 8.8 g (0.39 mol) of crude 2-methoxyethyl α-(hydroxyimino)-2-phenylacetate and 5.98 g of triethylamine in 65 ml tetrahydrofuran is cooled in an ice bath, and 8.3 g (0.043 mol) of p-toluenesulfonic acid chloride dissolved in 18 ml of tetrahydrofuran are added dropwise over 30 minutes. The resulting suspension is stirred for 16 hours at room temperature and then poured onto ice/water. The mixture is extracted with ethyl acetate, the organic layer washed with diluted HCl and water and dried over magnesium sulfate. Evaporation of the solvent gives an orange oil which is purified by chromatography on silica gel (eluent hexane/ethyl acetate 3:1). 12.68 g (86%) 2-Methoxyethyl α-(4-methylphenylsulfonyloxyimino)-2-phenylacetate are thus obtained as a colorless liquid. According to ¹H-NMR-analysis, the product is a mixture of 72% of the trans isomer and 28% of the cis isomer.

¹H-NMR (CDCl₁₃), δ [ppm]: 7.90 (d, 2 aromatic H); 7.55 (d, 2 aromatic H); 7.5–7.3 (m, 5 aromatic H): 4.55 and 4.38 (dxd, 2H, trans and cis COOCH₂—); 3.66 and 3.61 (dxd, 2H, trans and cis —CH₂—O—); 3.38 and 3.36 (s, 3H, CH₃O); 2.42 and 2.40 (s, 3H, CH₃–C₆H₄—).

| Elemental analysis: C₁₈H₁₉NO₆S (376.4) | | | | |
|---|---|---|---|---|
| | C [%] | H [%] | N [%] | S [%] |
| calculated | 57.28 | 5.07 | 3.71 | 8.49 |
| found | 57.27 | 5.08 | 3.58 | 8.54 |

Example 2

Preparation of hexyl α-(4-methylphenylsulfonyloxyimino)-2-phenylacetate 2.1 Hexyl phenylglyoxalate 16.42 g (0.1 mol) of methyl phenylglyoxalate is transesterified as described in example 1.1, using 1-hexanol instead of methoxyethanol. 21.33 g (87%) hexyl phenylglyoxalate are obtained as a colorless liquid.

¹H-NMR (CDCl₁₃), δ [ppm]: 7.98 (m, 2 aromatic H); 7.64 (m, 1 aromatic H); 7,50–7.45 (m, 2 aromatic H); 4.36 (t; 2H, COOCH₂—); 1.8–1.65 (m, 2H); 1.50–1.30 (m, 6H); 0.86 (t, 3H).

2.2 Hexyl α-(hydroxyimino)-2-phenylacetate 17.4 9 (0.074 mol) of hexyl phenylglyoxalate are reacted with 5.66 g (0.084 mol) of hydroxylammonium hydrochloride as described in example 1.2. Yield: 18.1 g (97%) of crude hexyl α-(hydroxyimino)-2-phenylacetate as a yellowish liquid. This compound is used without further purification in the next step.

¹H-NMR (CDCl₃), δ [ppm]: 7.60–7.25 (m, 5 aromatic H); 4.38 and 4.27 (t, 2H, trans and cis COOCH₂; 1.85-1-65 (m, 2H); 1.45–1.20 (m, 6H); 0.87 (t, 3H). The trans/cis isomer ratio is approximately 3:1.

2.3 Hexyl α-(4-methylphenylsulfonyloxyimino)-2-phenylacetate 18.0 g (0.0722 mol) of hexyl α-(hydroxyimino)-2-phenylacetate are reacted with 15.1 g of p-toluenesulfonic acid chloride as described in example 1.3 to give 23.2 g (80%) of hexyl α-(4-methylphenylsulfonyloxyimino)-2-phenylacetate as a colorless liquid after purification by chromatography. According to ¹H-NMR-analysis, the product is a mixture of 69% of the trans isomer and 31% of the cis isomer.

¹H-NMR (CDCl₃), δ [ppm]: 7.89 (d, 2 aromatic H); 7.55–7.75 (d and m, 7 aromatic H); 4.38 and 4.24 (t, 2H, trans and cis COOCH₂); 2.43 and 2.41 (s, 3H, CH₃–C₆H₄—); 1,73 (m, 2H); 1.4–1.15 (m, 6H); 0.88 (t, 3H).

| Elemental analysis: C₂₁H₂₅NO₅S (403.5) | | | | |
|---|---|---|---|---|
| | C [%] | H [%] | N [%] | S [%] |
| calculated | 62.51 | 6.25 | 3.47 | 7.95 |
| found | 62.66 | 6.34 | 3.50 | 8.11 |

Examples 3–33

The following examples 3–33 are prepared from the corresponding starting materials as described in examples 1 and 2. If not otherwise indicated, the products are mixtures of isomers with a trans/cis ratio of approximately 7:3. The structures and physical data are collected in table 1.

TABLE 1

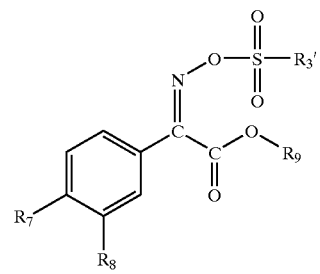

| | | | | | | Analysis [%] calc. Found | | | |
|---|---|---|---|---|---|---|---|---|---|
| ex. | R₇ | R₈ | R₉ | R₃' | physical properties | C | H | N | S |
| 3 | H | H | CH₃ | CH₃ | colorless viscous liquid trans/cis 58:42 | 46.69 46.81 | 4.31 4.32 | 5.44 5.20 | 12.46 12.33 |
| 4 | H | H | CH₃ | CH₃ | colorless viscous liquid trans/cis 93:7 | 46.69 46.97 | 4.31 4.54 | 5.44 5.31 | 12.46 11.23 |

TABLE 1-continued

| | | | | | | | | | |
|---|---|---|---|---|---|---|---|---|---|
| 5 | H | H | n-C$_3$H$_7$ | p-tol* | colorless liquid trans/cis 91:9 | 59.82 | 5.30 | 3.88 | 8.87 |
| | | | | | | 59.81 | 5.38 | 4.03 | 8.90 |
| 6 | H | H | n-C$_3$H$_7$ | p-tol* | colorless solid, mp 60–83° C. trans/cis 35:65 | 59.82 | 5.30 | 3.88 | 8.87 |
| | | | | | | 59.79 | 5.34 | 3.88 | 8.88 |
| 7 | H | H | i-C$_3$H$_7$ | p-tol* | colorless viscous liquid | 59.82 | 5.30 | 3.88 | 8.87 |
| | | | | | | 59.89 | 5.30 | 3.80 | 8.86 |
| 8 | H | H | i-C$_3$H$_7$ | p-tol* | colorless solid mp. 79–105° C. trans/cis 27:30 | 59.82 | 5.30 | 3.88 | 8.87 |
| | | | | | | 59.89 | 5.28 | 3.73 | 8.95 |
| 9 | H | H | n-C$_4$H$_9$ | p-tol* | colorless liquid | 60.78 | 5.64 | 3.73 | 8.54 |
| | | | | | | 60.92 | 5.62 | 3.60 | 8.47 |
| 10 | CH$_3$ | H | C$_2$H$_5$ | p-tol* | colorless wax | 59.82 | 5.30 | 3.88 | 8.87 |
| | | | | | | 59.85 | 5.50 | 3.79 | 8.91 |
| 11 | CH$_3$ | H | n-C$_3$H$_7$ | p-tol* | colorless crystals, mp 80–83° C. | 60.78 | 5.64 | 3.73 | 8.54 |
| | | | | | | 60.68 | 5.65 | 3.78 | 8.55 |
| 12 | CH$_3$ | H | n-C$_3$H$_7$ | CH$_3$ | colorless solid | 60.78 | 5.64 | 3.73 | 8.54 |
| | | | | | | 60.68 | 5.65 | 3.78 | 8.55 |
| 13 | CH$_3$ | H | n-C$_4$H$_9$ | p-tol* | colorless viscous liquid | 61.68 | 5.95 | 3.60 | 8.23 |
| | | | | | | 61.64 | 6.00 | 3.60 | 8.22 |
| 14 | CH$_3$ | H | CH$_3$O—C$_2$H$_4$ | p-tol* | colorless viscous liquid | 58.30 | 5.41 | 3.58 | 8.19 |
| | | | | | | 58.35 | 5.45 | 3.63 | 8.22 |
| 15 | C$_2$H$_5$ | H | C$_2$H$_5$ | p-tol* | colorless viscous liquid | 60.78 | 5.64 | 3.73 | 8.54 |
| | | | | | | 60.69 | 5.76 | 3.79 | 8.66 |
| 16 | C$_2$H$_5$ | H | C$_2$H$_5$ | p-tol* | colorless solid mp. 83–86° C. cis isomer | 60.78 | 5.64 | 3.73 | 8.54 |
| | | | | | | 60.56 | 5.60 | 3.81 | 8.59 |
| 17 | n-C$_4$H$_9$ | H | C$_2$H$_5$ | p-tol* | colorless viscous liquid | 62.51 | 6.25 | 3.47 | 7.95 |
| | | | | | | 62.49 | 6.28 | 3.70 | 7.84 |
| 18 | n-C$_4$H$_9$ | H | C$_2$H$_5$ | CH$_3$ | colorless liquid | 55.03 | 6.46 | 4.28 | 9.79 |
| | | | | | | 55.93 | 6.89 | 4.30 | 9.25 |
| 19 | F | H | C$_2$H$_5$ | p-tol* | yellowish liquid | 55.88 | 4.41 | 3.83 | 8.78 |
| | | | | | | 55.54 | 4.65 | 3.76 | 8.91 |
| 20 | CH$_3$O | H | C$_2$H$_5$ | p-tol* | viscous yellowish liquid | 57.28 | 5.07 | 3.71 | 8.49 |
| | | | | | | 57.04 | 5.24 | 3.75 | 8.39 |
| 21 | CH$_3$O | CH$_3$O | C$_2$H$_5$ | p-tol* | viscous yellowish liquid | 56.01 | 5.19 | 3.44 | 7.87 |
| | | | | | | 55.24 | 5.32 | 3.35 | 7.60 |
| 22 | CH$_3$O | CH$_3$O | CH$_3$O—C$_2$H$_4$— | p-tol* | viscous yellowish liquid | 54.91 | 5.30 | 3.20 | 7.33 |
| | | | | | | 54.62 | 5.94 | 2.98 | 6.51 |
| 23 | CH$_3$O | CH$_3$O | CH$_3$O—C$_2$H$_4$— | CH$_3$ | solid beige trans/cis 95:5 | 46.53 | 5.30 | 3.88 | 8.87 |
| | | | | | | 46.52 | 5.24 | 3.84 | 8.98 |
| 24 | CH$_3$S | H | CH$_3$ | p-tol* | yellowish solid, mp. 113–120° C. trans/cis 22:78 | 53.81 | 4.52 | 3.69 | 16.90 |
| | | | | | | 53.70 | 4.84 | 3.64 | 16.95 |
| 25 | CH$_3$S | H | CH$_3$ | p-tol* | yellowish viscous liquid trans/cis 93:7 | 53.81 | 4.52 | 3.69 | 16.90 |
| | | | | | | 53.80 | 4.61 | 3.61 | 16.92 |
| 26 | CH$_3$S | H | CH$_3$ | CH$_3$ | yellowish solid mp. 72–91° C. trans/cis 93:7 | 43.55 | 4.32 | 4.62 | 21.14 |
| | | | | | | 43.63 | 4.30 | 4.61 | 21.43 |
| 27 | CH$_3$S | H | C$_2$H$_5$ | p-tol* | yellowish viscous liquid | 54.95 | 4.87 | 3.56 | 16.30 |
| | | | | | | 55.14 | 4.79 | 3.55 | 16.38 |
| 28 | CH$_3$S | H | CH$_3$O—C$_2$H$_4$— | p-tol* | yellowish viscous liquid | 53.89 | 5.00 | 3.31 | 15.14 |
| | | | | | | 54.00 | 4.95 | 3.36 | 15.08 |
| 29 | CH$_3$S | H | CH$_3$O—C$_2$H$_4$— | CH$_3$ | yellowish viscous liquid | 44.95 | 4.93 | 4.03 | 18.46 |
| | | | | | | 45.07 | 5.06 | 3.91 | 18.66 |
| 30 | n-C$_4$H$_9$S | n-C$_4$H$_9$S | C$_2$H$_5$ | p-tol* | reddish viscous liquid | 57.34 | 6.35 | 2.67 | 18.36 |
| | | | | | | 57.64 | 6.44 | 2.68 | 18.44 |
| 31 | (CH$_3$)$_2$N | H | C$_2$H$_5$ | p-tol* | orange solid mp. 148–151° C. | 58.45 | 5.68 | 7.17 | 8.21 |
| | | | | | | 58.20 | 5.87 | 7.45 | 8.47 |
| 32 | CH$_3$O | CH$_3$O | C$_2$H$_5$ | CH$_3$ | yellowish solid mp. 84–87° C. | 47.12 | 5.17 | 4.23 | 9.68 |
| | | | | | | 46.78 | 5.03 | 4.11 | 9.97 |
| 33 | CH$_3$S | H | C$_2$H$_5$ | CH$_3$ | yellowish solid mp. 51–63° C. | 45.41 | 4.76 | 4.41 | 20.20 |
| | | | | | | 45.37 | 4.89 | 4.41 | 20.22 |

*p-tol is

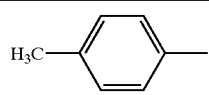

Example 34

Preparation of ethyl α-(4-methylphenylsulfonyloxyimino)-2-(thianthren-2-yl)-acetate

34.1 Ethyl 2-(thianthren-2-yl)-α-keto-acetate 29.3 g (0.22 mol) of $AlC1_3$ are added portionwise to a solution of 21.6 g (0.1 mol) of thianthrene and 28.7 g (0.21 mol) of ethyl oxalic acid chloride in 150 ml methylenechloride at 0° C. The resulting solution is stirred during two hours at room temperature and subsequently poured onto water. The product is extracted with methylenechloride, the organic solution dried over magnesium sulfate and the solvent evaporated. The residue is purified by chromatography on silica gel (eluent: petroleum ether/ethyl acetate 7:1) to give 13 g (41%) of 2-(thianthren-2-yl)-α-keto-acetate as viscous yellowish oil.

$^1$H-NMR (CDCl$_3$), δ [ppm]: 8.08 (d, 1 aromatic H); 7.86 (dxd, 1 aromatic H); 7.55 (d, 1 aromatic H); 7.45 (m, 2 aromatic H); 7.25 (m, 2 aromatic H); 4.43 (q, 2H); 1.39 (t, 3H).

34.2 Ethyl 2-(thianthren-2-yl)-α-(hydroxyimino)-acetate

As described in example 1.2, 7.7 g (0.024 mol) of 2-(thianthren-2-yl)-α-keto-acetate are reacted with 1.85 g (0.0267 mol) of hydroxylammonium hydrochloride in pyridine to give 7.5 g (94%) of crude 2-(thianthren-2-yl)-α-(hydroxyimino)-acetate, which is used without further purification for the next reaction step.

$^1$H-NMR (CDCl$_3$), δ[ppm]: 7,65–7.15 (m 7 aromatic H); 4.44 and 4.35 (q, 2H); 1.37 and 1.33 (t,3H).

34.3 Ethyl α-(4-methylphenylsulfonyloxyimino)-2-(thianthren-2-yl)-acetate 9.5 g (0.029 mol) of ethyl 2-(thianthren-2-yl)-o-(hydroxyimino)-acetate are reacted with 6.0 g (0.034 mol) of p-toluenesulfonic acid chloride as described in example 1.3 to give, after purification by chromatography (silica gel, eluent white spirit/ethyl acetate 4:1), 8.2 g (59%) of ethyl α-(4-methylphenylsulfonyloxyimino)-2-(thianthren-2-yl)-acetate as a yellow viscous liquid.

| Elemental analysis: C$_{23}$H$_{19}$NO$_5$S$_3$ (485.60): | | | | |
|---|---|---|---|---|
| | C [%] | H [%] | N [%] | S [%] |
| calculated | 56.89 | 3.94 | 2.88 | 19.81 |
| found | 56.89 | 4.13 | 2.96 | 19.64 |

Example 35

Methylsulfonyloxyimino-3,4-dimethoxyphenyl acetic acid 2-[2-(methylsulfonyl-oxyimino-3,4-dimethoxyphenyl-acetoxy)-ethoxy]-ethyl ester

35.1 3,4-Dimethoxy-phenyl)-oxo-acetic acid 2-{2-[(3,4-dimethoxy-phenyl)-oxo-acetoxy]-ethoxy}-ethyl ester This product is obtained in 45% yield by transesterification of phenylglyoxalate with 2-(2-hydroxy-ethoxy)-ethanol instead of 2-methoxyethanol as described in example 1.1. The crude product is used for the next reaction step without further purification

35.2 Hydroxyimino-3,4-dimethoxyphenyl acetic acid 2-[2-(hydroxyimino-3,4-dimethoxy-phenyl-acetoxy)-ethoxy]-ethyl ester 48.0 g (0.1 mol) of (3,4-Dimethoxy-phenyl)-oxo-acetic acid 2-{2-[(3,4-dimethoxy-phenyl)-oxo-acetoxy]-ethoxy}-ethyl ester are transformed into hydroxyimino-3,4-dimethoxyphenyl acetic acid 2-[2-(hydroxyimino-3,4-dimethoxyphenyl-acetoxy)-ethoxy]-ethyl ester by treatment with 14.97 g (0.21 mol) of hydroxylammonium hydrochloride in pyridin as described in example 1.2. 33.25 g (65%) of the crude product are obtained as a beige solid and used in the next reaction step without further purification.

35.3 Methylsulfonyloxyimino-3,4-dimethoxyphenyl acetic acid 2-[2-(methylsulfonyloxyimino-3,4-dimethoxyphenyl-acetoxy)-ethoxy]-ethyl ester 10.4 g (0.02 mol) of Hydroxyimino-3,4-dimethoxyphenyl acetic acid 2-[2-(hydroxyimino-3,4-dimethoxyphenyl-acetoxy)-ethoxy]-ethyl ester are reacted with 5.0 g (0.44 mol) of methylsulfonyl chloride in 100 ml of pyridine as described in example 1.3. After isolation and chromatography on silicagel, 7.1 g (53%) of 2-[2-(methylsulfonyloxyimino-3,4-dimethoxyphenylacetoxy)-ethoxy]-ethyl ester are obtained as a sticky yellowish solid. According to the $^1$H-NMR spectrum, the product consists of two major trans/cis in a ratio of 3:1 and contains residues of solvent.

$^1$H-NMR (CDCl$_3$), δ [ppm]: 7.25 (dxd, 2 aromatic H), 7.10 (dxd, 2 aromatic H); 6.85 (dxd, 2 aromatic H); 4.6 and 4.55 (t, 4 H); 3,89 and 3,88 (s, 12 H, CH$_3$O); 3.84 (m, 4 H); 3.20 and 3.18 (s, 6H).

| Elemental analysis: C$_{26}$H$_{32}$N$_2$O$_{15}$S$_2$ (676.67) | | | | |
|---|---|---|---|---|
| | C [%] | H [%] | N [%] | S [%] |
| calculated | 46.15 | 4.77 | 4.14 | 9.48 |
| found | 47.18 | 5.10 | 4.12 | 8.27 |

Example 36

Preparation of N,N-diethyl α-(4-methylphenylsulfonyloxyimino)-2-phenylacetylamide

36.1 N,N-diethyl α-keto-2-phenylacetylamide 23 g (0.2 mol) of Dichloromethyl-methylether are added dropwise to 30 g (0.2 mol) of phenylglyoxylic and the resulting suspension is stirred for 2 hours. The yellowish solution is than cooled in an ice bath, and 44 g (0.6 mol) of diethylamine are added dropwise while stirring. The reaction mixture is stirred overnight, poured on water/ice and extracted with dichloromethane. The organic solution is washed with diluted HCl, dried over magnesium sulfate and the solvent is evaporated. The resulting reddish liquid is filtered over silicagel (eluent:hexane/ethyl acetate 3:1) to give 39.8 g (97%) of N,N-diethyl α-keto-2-phenylacetylamide as a yellowish liquid after evaporation of the solvent. The crude product is used without further purification in the next step.

Elemental analysis: $C_{12}H_{15}NO_2$ (205.26):

|  | C [%] | H [%] | N [%] |
|---|---|---|---|
| calculated | 70.22 | 7.37 | 6.82 |
| found | 69.40 | 7.47 | 6.15 |

36.2 N,N-diethyl α-(hydroxyimino)-2-phenylacetylamide 26.0 g (0.126 mol) of N,N-diethyl α-keto-2-phenylacetylamide and 9.6 g (1.39 mol) of hydroxylamine-hydrochloride are dissolved in 250 ml of pyridine and the resulting solution is stirred at room temperature for 12 hours and subsequently heated to 60° C. for another 6 hours. After cooling to room temperature, ethyl acetate and water are added, the organic layer is separated and washed several times with diluted HCl and water. After drying and evaporation of the solvent, 25.9 g (93%) of crude N,N-diethyl α-(hydroxyimino)-2-phenylacetylamide are obtained as a sticky yellowish solid.

$^1$H-NMR (CDCl$_3$), δ [ppm]:7.65–7.50 (m, 2 aromatic H); 7.40–7.25 (m, 3 aromatic H); 3.56 (q, 2H); 3.20 (q, 2H); 1.24 (t, 3H); 1.03 (t, 3H).

36.3 N,N-diethyl α-(4-methylphenylsulfonyloxyimino)-2-phenylacetylamide 11.44 g (0.06 mol) of p-toluenesulfonic acid chloride dissolved in 25 ml of tetrafydrofuran (THF) are dropwise added to a solution of 12 g (0.055 mol) of α-(hydroxyimino)-2-phenylacetylamide and 8.3 g (0.082 mol) of triethylamine in 90 ml of THF at 0° C. When the addition is complete, the reaction mixture is stirred at 0° C. for another hour and than at room temperature over night. Ethyl acetate and water are added to the mixture, the organic layer is separated and washed several times with diluted HCl and water. The solution is dried over magnesium sulfate, the solvent evaporated and the remaining red oil purified by chromatography on silica gel (eluent: petroleum ether/ethyl acetate 4:1. 10.57 g (52%) of N,N-diethyl α-(4-methylphenylsulfonyloxyimino)-2-phenylacetylamide are thus obtained as a colorless solid, mp. 73–75° C.

Elemental analysis: $C_{19}H_{22}N_2O_4S$ (374.5)

|  | C [%] | H [%] | N [%] | S [%] |
|---|---|---|---|---|
| calculated | 60.94 | 5.92 | 7.48 | 8.56 |
| found | 61.01 | 6.02 | 7.36 | 8.60 |

Examples 37–39

The following examples 37–39 are prepared from the corresponding starting materials as described in example 36. The structures and physical data are listed in table 2.

TABLE 2

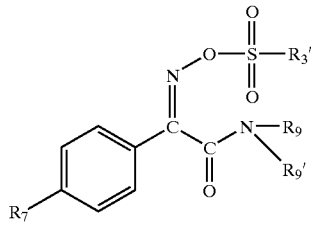

| ex. | $R_7$ | $R_3'$ | $R_9$ | $R_9'$ | physical properties | Analysis [%] calc. Found | | | |
|---|---|---|---|---|---|---|---|---|---|
|  |  |  |  |  |  | C | H | N | S |
| 37 | H | $CH_3$ | $C_2H_5$ | $C_2H_5$ | colorless solid, mp. 91–96° C. | 52.33 52.38 | 6.08 6.29 | 9.39 9.16 | 10.75 10.68 |
| 38 | H | p-tol* | $C_4H_9$ | $C_4H_9$ | yellowish solid, mp. 68–72° C. | 64.16 64.43 | 7.02 7.17 | 6.51 6.43 | 7.45 7.16 |
| 39 | $C_2H_5$ | p-tol* | $C_2H_5$ | $C_2H_5$ | yellowish viscous liquid | 62.66 62.61 | 6.51 6.47 | 6.96 6.87 | 7.97 8.06 |

*p-tol is

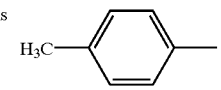

Example 40

Preparation of methyl α-(diethoxyphosphoryloxyimino)-2-phenylacetate 40.1 Methyl α-(hydroxyimino)-2-phenylacetate 41.0 g (0.25 mol) of methyl phenylglyoxalate are dissolved in 300 ml of pyridine. 19.1 g (0.27 mol) of hydroxylammonium hydrochloride are added in portions to this solution. When the addition is complete, the reaction mixture is stirred at room temperature for 20 hours. After addition of ethyl acetate and water, the organic layer is separated, washed with diluted HCl and water and dried over magnesium sulfate. Evaporation of the solvent gives 45 g (100%) of crude methyl α-(hydroxyimino)-2-phenylacetate as a slightly brownish liquid. This compound is used without further purification in the next reaction step. $^1$H-NMR (CDCl$_3$), δ [ppm]:7.55–7.30 (m, 5 aromatic H); 3.96 and 3.87 (s, 3H, CH$_3$O of the trans and cis isomers). The trans/cis isomer ratio is approximately 3:1.

40.2 Methyl-α-(diethoxyphosphoryloxyimino)-2-phenylacetate 25.1 g (0.14 mol) of Methyl α-(hydroxyimino)-2-phenylacetate, 14.2 g (0.14 mol) of triethylamine and a catalytic amount of 4-dimethylaminopyridine are dissolved in 300 ml of CH$_2$Cl$_2$. 24.16 g (0.14 mol) of diethylchlorophosphate are added dropwise to the resulting solution with stirring. The reaction mixture is stirred overnight and subsequently poured on ice/water. The resulting suspension is extracted with dichloromethane and the organic solution dried over magnesium sulfate. Evaporation of the solvent gives an oil, which is further purified by flash chromatography (silicagel, eluent petroleum ether/ethyl acetate 2:1). 10.5 g (24%) of α-(diethoxyphosphoryloxyimino)-2-phenylacetate are thus obtained as a slightly yellowish liquid.

$^{31}$P-NMR (CDCl$_3$), δ[ppm], reference H$_3$PO$_4$: –0.11 and –0.66 ppm (P of the cis and trans isomers).

| Elemental analysis: $C_{13}H_{18}NO_6P$ (315.27) | | | |
|---|---|---|---|
| | C [%] | H [%] | N [%] |
| calculated | 49.53 | 5.75 | 4.44 |
| found | 49.72 | 5.98 | 4.60 |

Examples 41–44

The following examples 41–44 are prepared from the corresponding starting materials as described for examples 40. The structures and physical data are given in table 3. If not otherwise indicated, the products are mixtures of isomers with a trans/cis ratio of approximately 7:3.

TABLE 3

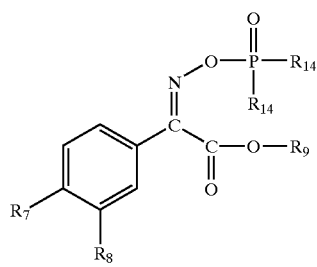

| ex. | $R_7$ | $R_8$ | $R_9$ | $R_{14}$ | physical properties | Analysis [%] calc. Found | | | |
|---|---|---|---|---|---|---|---|---|---|
| | | | | | | C | H | N | S |
| 41 | H | H | $C_3H_7$ | $OC_2H_5$ | colorless liquid | 52.48 | 6.46 | 4.08 | — |
| | | | | | | 52.51 | 6.61 | 4.11 | |
| 42 | $CH_3O$ | $CH_3O$ | $CH_3O-C_2H_4O-$ | $OC_2H_5$ | viscous yellowish | 49.36 | 6.21 | 3.60 | — |
| | | | | | liquid | 49.36 | 6.16 | 3.49 | |
| 43 | $CH_3S$ | H | $C_2H_5$ | $OC_2H_5$ | yellowish liquid | 48.00 | 5.91 | 3.73 | 8.54 |
| | | | | | | 48.03 | 6.09 | 3.65 | 8.78 |
| 44 | H | H | $C_3H_7$ | tol* | yellowish resin | 68.96 | 6.02 | 3.22 | — |
| | | | | | | 68.68 | 6.10 | 3.25 | |
| 45 | $CH_3S$ | H | $CH_3$ | $OC_2H_5$ | viscous yellowish | 46.54 | 5.58 | 3.88 | 8.87 |
| | | | | | liquid | 46.35 | 5.72 | 3.80 | 8.54 |
| 46 | $CH_3S$ | H | $CH_3O-C_2H_4-$ | $OC_2H_5$ | viscous yellowish | 47.40 | 5.97 | 3.46 | 7.91 |
| | | | | | liquid | 47.08 | 6.10 | 3.55 | 7.64 |

*tol is $H_3C-C_6H_4-$

B) Application Examples

Example 47

Preparation of Poly(benzylmethacrylate-co-methacrylic acid)

24 g of benzylmethacrylate, 6 g of methacrylic acid and 0.525 g of azobisisobutyronitrile (AIBN) are dissolved in 90 ml of propylene glycol 1-monomethyl ether 2-acetate (PGMEA). The resulting reaction mixture is placed in a preheated oil bath at 80° C. After stirring for 5 hours at 80° C. under nitrogen, the resulting viscous solution is cooled to room temperature and used without further purification. The solid content is about 25%.

In the following application examples the photoinitiators collected in table 4 and the coinitiators collected in table 5 are employed.

TABLE 4

Photoinitiators evaluated

| Photoinitiator No. | Structure |
|---|---|
| P-1 | 3,4-dimethylphenyl-C(CN)=N-O-SO₂-CH₃ |
| P-2 | 4-methoxyphenyl-C(CN)=N-O-SO₂-CH₃ |
| P-3 | 4-(methylthio)phenyl-C(CN)=N-O-SO₂-(4-methylphenyl) |
| P-4 | 3,4-bis(methylthio)phenyl-C(CN)=N-O-SO₂-CH₃ |
| P-5 | PhCH₂-C(CN)=N-O-SO₂-CH₃ |
| P-6 | Ph-CH=CH-C(O)-C(CN)=N-O-SO₂-CH₃ |
| P-7 | 2-methylphenyl-C(CN)=C(thiophene-5-yl)=N-O-SO₂-CH₃ |

TABLE 4-continued
Photoinitiators evaluated
| Photoinitiator No. | Structure |
|---|---|
| P-8 | 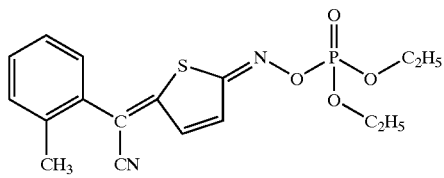 |
| P-9 | 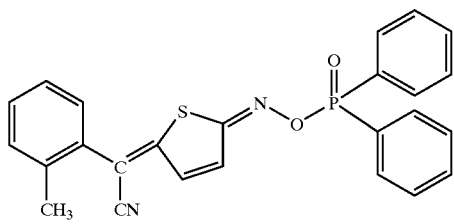 |
| P-10 compound of example 1 | 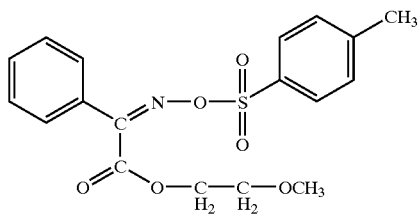 |
| P-11 compound of example 2 | 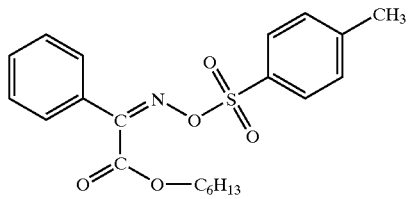 |
| P-12 compound of example 40 | 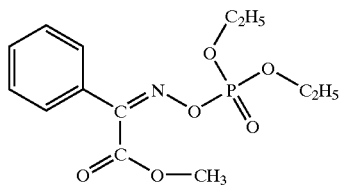 |

TABLE 5

Coinitiators applied

| No. | | Structure |
|---|---|---|
| C-1 | 4,4'-Bis(diethylamino)-benzophenone | |
| C-2 | Coumarin 106 | |
| C-3 | N-Phenylglycine | |

Example 48

A photocurable composition is prepared by mixing the following components:
200.0 parts by weight of a copolymer of benzylmethacrylate and methacrylic acid (benzylmethacrylate: methacrylic acid=80:20 by weight) 25% propylene glycol 1-monomethyl ether 2-acetate (PGMEA) solution, prepared in above example 47
50.0 parts by weight of dipentaerythritol hexaacrylate ((DPHA), provided by UCB Chemicals),
2.0 parts by weight of the photoinitiator,
1.2 parts by weight of the coinitiator, and
150.0 parts by weight of PGMEA All operations are carried out under yellow light. The compositions are applied to an aluminum plate using an electric applicator with a wire wound bar. The solvent is removed by heating at 100° C. for 2 minutes in a convection oven. The thickness of the dry film is approximately 2 μm. To this coating an acetate film is applied, over which a standardized test negative with 21 steps of different optical density (Stouffer step wedge) is placed. The sample is covered with a second UV-transparent film and pressed onto a metal plate by means of vacuum. Exposure is carried out in a first test series for 5 seconds, in a second series for 10 seconds and in a third series for 20 seconds, using a 3 kW metal halide lamp (ORC, model SMX 3000) at a distance of 60 cm. After exposure, the cover films and the mask are removed and the exposed film is developed with 1% sodium carbonate aqueous solution for 200 sec. at 30° C. by using a spray type developer (Walter Lemmen, model T21). The sensitivity of the initiator system used is characterized by indicating the highest number of the steps which completely remain (i.e. polymerize) after developing. The higher the number of steps, the more sensitive is the tested system. The used photoinitiators and coinitiators as well as the results are collected in table 6.

TABLE 6

Test results example 48

| Photoinitiator | Coinitiator | Sensitivity - number of cured steps after | | |
|---|---|---|---|---|
| | | 5 sec | 10 sec | 20 sec |
| P-3 | C-1 | 4 | 7 | 9 |
| P-3 | C-2 | 5 | 8 | 11 |
| P-4 | C-1 | 7 | 9 | 11 |
| P-6 | C-1 | 6 | 8 | 10 |
| P-7 | C-1 | 7 | 9 | 11 |
| P-7 | C-2 | 6 | 8 | 10 |
| P-8 | C-1 | 5 | 7 | 9 |
| P-9 | C-1 | 6 | 8 | 10 |
| P-12 | C-1 | 3 | 6 | 9 |
| P-13 | C-1 | 8 | 11 | 13 |

P-13 is

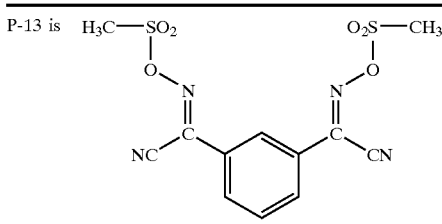

Example 49

The photosensitive composition used in example 48 is applied for the following sensitivity test. All operations are carried out under yellow light. The compositions are applied to an aluminum plate using an electric applicator with a wire wound bar. The solvent is removed by heating at 100° C. for 2 minutes in a convection oven. The thickness of the dry film is approximately 2 μm. To this coating an acetate film is applied, over which a standardized test negative with 21 steps of different optical density (Stouffer step wedge) is placed. The sample is covered with a second UV-transparent film and pressed onto a metal plate by means of vacuum. Interference filters are placed on the top to select the wavelengths at 365 nm, 405 nm, and 436 nm. Exposure is carried out using a 3 kW metal halide lamp (ORC, model SMX 3000) at a distance of 60 cm. After exposure, the cover films and the mask are removed and the exposed film is developed with 1% sodium carbonate aqueous solution for 200 sec. at 30° C. by using a spray type developer (Walter Lemmen, model T21). The sensitivity of the initiator system used is characterized by the minimum dose required to cure upon irradiation at each wavelength, which is calculated from the transmittance of the step with the highest number that is cured. The smaller the dose, the more sensitive is the tested initiatior system at the selected wavelength. The used initiator system as well as the results are collected in table 7

TABLE 7

Test results example 49

| Photoinitiator | Coinintiator | Sensitivity [mJ/cm$^2$] | | |
|---|---|---|---|---|
| | | at 365 nm | at 405 nm | at 436 nm |
| P-1 | C-1 | 26 | 76 | 463 |
| P-2 | C-1 | 26 | 76 | 463 |
| P-3 | C-1 | 36 | 151 | 463 |
| P-3 | C-2 | 73 | 151 | 463 |
| P-3 | C-3 | 18 | 151 | >650 |
| P-4 | C-1 | 13 | 19 | 82 |
| P-5 | C-1 | 103 | 214 | >650 |
| P-6 | C-1 | 18 | 38 | 116 |
| P-7 | C-1 | 18 | 54 | 163 |
| P-7 | C-2 | 36 | 38 | 58 |
| P-8 | C-1 | 26 | 54 | 82 |
| P-9 | C-1 | 18 | 54 | 82 |
| P-10 | C-1 | 52 | 107 | 463 |
| P-11 | C-1 | 52 | 151 | 463 |
| P-12 | C-1 | 73 | 107 | 463 |
| P-13 | C-1 | 9 | 19 | 82 |

Example 50

A photocurable composition is prepared by mixing the following components:
100.0 parts by weight of IRR222 (water soluble urethane acrylate/DTMPTA*$^1$/TPGDA*$^2$=80/11/9, provided by Daicel UCB)
0.5 parts by weight of the photoinitiator
0.5 parts by weight of the coinitiator C-1
33.3 parts by weight of acetone
*$^1$ DTMPTA is di(trimethylolpropane) tetraacrylate
*$^2$ TPGDA is tri(propylene glycol) diacrylate The compositions are applied to an aluminum plate using an electric applicator with a wire wound bar. The solvent is removed by heating at 60° C. for 15 minutes in a convection oven. The thickness of the dry film is approximately 30 μm. To this coating an acetate film is applied, over which a standardized test negative with 21 steps of different optical density (Stouffer step wedge) is placed. The sample is covered with a second UV-transparent film and pressed onto a metal plate by means of vacuum. Exposure is carried out in a first test series for 5 seconds, in a second series for 10 seconds and in a third series for 20 seconds, using a 3 kW metal halide lamp (ORC, model SMX 3000) at a distance of 60 cm. After exposure, the cover films and the mask are removed and the exposed film is developed with water for 15 sec. at 30° C. by using a spray type developer (Walter Lemmen, model T21). The sensitivity of the initiator system used is characterized by indicating the highest number of the steps which completely remain (i.e. polymerize) after developing. The higher the number of steps, the more sensitive is the system tested. The tested initiator/coinitiator as well as the test results are collected in table 8.

TABLE 8

Test results example 50

| Photoinitiator | Sensitivity | | |
|---|---|---|---|
| | 5 sec | 10 sec | 20 sec |
| P-1 | 4 | 6 | 8 |
| P-2 | 4 | 6 | 8 |
| P-3 | 3 | 5 | 7 |
| P-4 | 4 | 5 | 7 |

What is claimed is:
1. A radically photopolymerizable composition comprising
(a) at least one polymer or oligomer having at least two ethylenically unsaturated groups and at least one carboxyl function within the molecule structure;
(b) as photoinitiator, at least one compound of the formula I, II, III, and IV

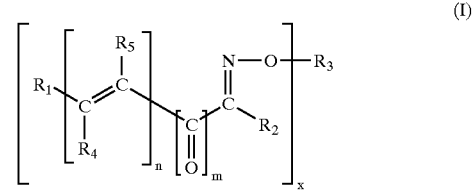

(I)

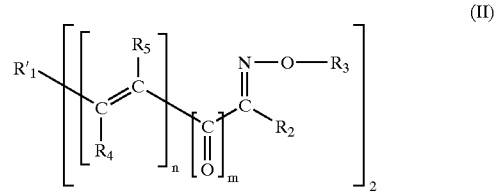

(II)

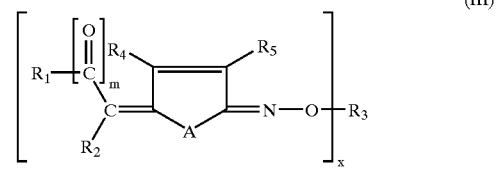

(III)

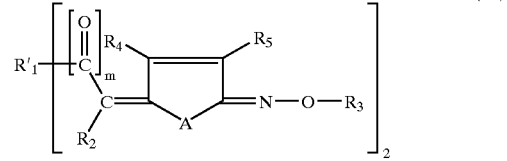

(IV)

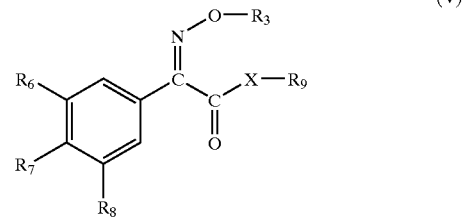

(V)

-continued

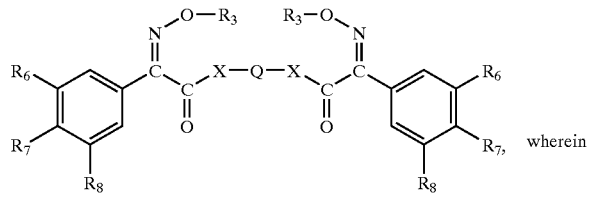
(VI)

wherein m is 0 or 1;

n is 0, 1, 2 or 3;

x is 1 or 2;

$R_1$ is phenyl, phenyl which is substituted by one or more of the radicals $C_1$–$C_{12}$alkyl, $C_1$–$C_4$-haloalkyl, halogen, phenyl, $OR_{10}$, $NR_{11}R_{12}$, $SR_{13}$ and/or —S-phenyl, it being possible for the substituents $OR_{10}$, $SR_{13}$ and $NR_{11}R_{12}$ to form 5- or 6-membered rings, via the radicals $R_{10}$, $R_{11}$, $R_{12}$ and/or $R_{13}$, with further substituents on the phenyl ring or with one of the carbon atoms of the phenyl ring, or $R_1$ is naphthyl, anthracyl or phenanthryl, the radicals naphthyl, anthracyl and phenanthryl being unsubstituted or substituted by $C_1$–$C_6$alkyl, phenyl, $OR_{10}$, $NR_{11}R_{12}$, $SR_{13}$ and/or —S-phenyl, it being possible for the substituents $OR_{10}$, $SR_{13}$ and $NR_{11}R_{12}$ to form 5- or 6-membered rings, via the radicals $R_{10}$, $R_{11}$, $R_{12}$ and/or $R_{13}$ with further substituents on the naphthyl, anthracyl or phenanthryl ring or with one of the carbon atoms of the naphthyl, anthracyl or phenanthryl ring, or $R_1$ is a heteroaryl radical which is unsubstituted or substituted by $C_1$–$C_6$alkyl, phenyl, $OR_{10}$, $NR_{11}R_{12}$, $SR_{13}$ and/or —S-phenyl, it being possible for the substituents $OR_{10}$, $SR_{13}$ and $NR_{11}R_{12}$ to form 5- or 6-membered rings, via the radicals $R_{10}$, $R_{11}$, $R_{12}$ and/or $R_{13}$ with further substituents on the heteroaryl ring or with one of the carbon atoms of the heteroaryl ring; or $R_1$ is $C_2$–$C_{12}$alkenyl, $C_4$–$C_8$cycloalkenyl, or $C_6$–$C_{12}$bicycloalkenyl, or, if m is zero, $R_1$ in the formula I additionally is benzoyl, 2-furoyl, 2-thiophenecarbonyl, 2-pyridinecarbonyl or 2-pyrrolecarbonyl, wherein the radicals benzoyl, 2-furoyl, 2-thiophenecarbonyl, 2-pyridinecarbonyl or 2-pyrrolecarbonyl are unsubstituted or substituted by one or more of the radicals $C_1$–$C_{12}$alkyl, $C_1$–$C_4$haloalkyl, halogen, phenyl, $OR_{10}$, $NR_{11}R_{12}$, $SR_{13}$ and/or —S-phenyl, it being possible for the substituents $OR_{10}$, $SR_{13}$ and $NR_{11}R_{12}$ to form 5- or 6-membered rings, via the radicals $R_{10}$, $R_{11}$, $R_{12}$ and/or $R_{13}$, with further substituents on the benzoyl, 2-furoyl, 2-thiophenecarbonyl, 2-pyridinecarbonyl or 2-pyrrolecarbonyl ring or with one of the carbon atoms of the benzoyl, 2-furoyl, 2-thiophenecarbonyl, 2-pyridinecarbonyl or 2-pyrrolecarbonyl ring;

or, if m is zero, n is 1 and simultaneously $R_5$ is phenyl which is unsubstituted or substituted by one or more $C_1$–$C_{12}$alkyl, $C_1$–$C_4$haloalkyl, halogen, phenyl, $OR_{10}$, $NR_{11}R_{12}$, $SR_{13}$ and/or —S-phenyl, $R_1$ in formula I additionally is hydrogen;

or, if m is 0 and n is 0, $R_1$ in formual I additionally is CN, hydrogen or $C_1$–$C_{12}$ alkyl, with the proviso that $R_1$ and $R_2$ are not simultaneously hydrogen or alkyl;

$R'_1$ is $C_2$–$C_{12}$alkylene, phenylene, naphthylene,

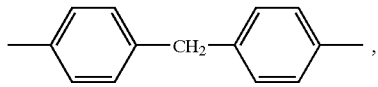, diphenylene or oxydiphenylene, these radicals are unsubstituted or substituted by $C_1$–$C_{12}$alkyl;

$R_2$ has one of the meanings of $R_1$ or is phenyl, CN-substituted phenyl, $C_2$–$C_6$alkanoyl, benzoyl which is unsubstituted or substituted by $C_1$–$C_6$alkyl, phenyl, $OR_{10}$, $SR_{13}$, $NR_{11}R_{12}$ and/or —S-phenyl, or $R_2$ is CN, phenoxycarbonyl, $NO_2$, $C_1$–$C_4$haloalkyl, $C_2$–$C_6$alkoxycarbonyl, $S(O)_y$—$C_1$–$C_6$alkyl, $S(O)_y$—$C_6$–$C_{12}$aryl, $C_1$–$C_{12}$alkyl-substituted $S(O)_y$—$C_6$–$C_{12}$aryl, $SO_2O$—$C_1$–$C_6$alkyl, $SO_2O$—$C_6$–$C_{10}$aryl, diphenylphosphinoyl or $NHCONH_2$, or, if m is 1, $R_1$ and $R_2$ together with the CO group may form a 5- or 6-membered ring which is unsubstituted or substituted by $C_1$–$C_6$alkyl, phenyl, $OR_{10}$, $SR_{13}$, $NR_{11}R_{12}$ and/or —S-phenyl, said ring may additionally be interrupted by —O—, —S—, —N($R_{11}$)— and/or by CO, and to said ring may be fused one or more benzo radicals;

y is 1 or 2;

$R_3$ if x is 1 is $C_1$–$C_{18}$alkylsulfonyl, phenyl-$C_1$–$C_3$alkylsulfonyl, camphorylsulfonyl, $C_1$–$C_{10}$haloalkylsulfonyl, phenylsulfonyl, naphthylsulfonyl, anthracylsulfonyl or phenanthrylsulfonyl, wherein the groups phenyl, naphthyl, anthracyl and phenanthryl of the radicals phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, $NO_2$, $C_1$–$C_{16}$alkyl, phenyl, $C_1$–$C_4$alkylthio, $OR_{10}$, $COOR_{13}$, $C_1$–$C_4$alkyl-OCO—, $R_{13}OSO_2$— and/or —$NR_{11}R_{12}$; or $R_3$ is $C_2$–$C_6$haloalkanoyl, halobenzoyl, or a group

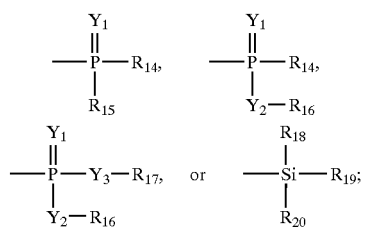

$R_3$ if x is 2, is $C_2$–$C_{12}$alkylenedisulfonyl, phenylenedisulfonyl, naphthylenedisulfonyl,

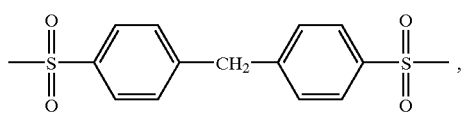, diphenylenedisulfonyl, or oxydiphenylenedisulfonyl, wherein the groups phenylene, naphthylene,

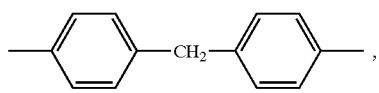

diphenylene and oxydiphenylene of the radicals phenylenedisulfonyl, naphthylenedisulfonyl,

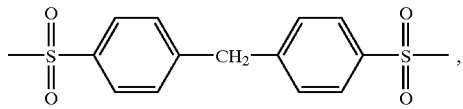

diphenylenedisulfonyl, or oxydiphenylenedisulfonyl are unsubstituted or substituted by $C_1$–$C_{12}$alkyl;

$R_4$ and $R_5$ are independently of each other hydrogen, halogen, $C_1$–$C_8$alkyl, $C_1$–$C_6$alkoxy, $C_1$–$C_4$haloalkyl, CN, $NO_2$, $C_2$–$C_6$alkanoyl, benzoyl, phenyl, —S-phenyl, $OR_{10}$, $SR_{13}$, $NR^{11}R_{12}$, $C_2$–$C_6$alkoxycarbonyl, phenoxycarbonyl, $S(O)_yC_1$–$C_6$alkyl, $S(O)_yC_6$–$C_{12}$aryl, $C_1$–$C_{12}$alkyl-substituted $S(O)_yC_6$–$C_{12}$aryl, $SO_2O$—$C_1$–$C_6$alkyl, $SO_2O$—$C_6$–$C_{10}$aryl or $NHCONH_2$, or $R_4$ and $R_5$ together are a direct bond or —$C(R_{21})$=$C(R_{22})$—$C(R_{23})$=$C(R_{24})$—;

A is —S—, —O—, —$NR_{10}$—, or a group of formula A1, A2, A3 or A4

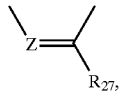 (A1)

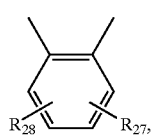 (A2)

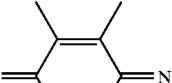 (A3)

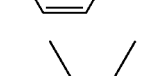 (A4)

Y, $Y_1$, $Y_2$ and $Y_3$ independently of one another are —O— or —S—;

Z is —$CR_{28}$— or —N—; and $Z_1$ is —$CH_2$—, —S—, —O— or —$NR_{10}$—;

$R_{10}$ is hydrogen, phenyl, $C_1$–$C_{12}$alkyl which is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl or $R_{10}$ is $C_2$–$C_{12}$alkyl interrupted by one or more —O—, said interrupted $C_2$–$C_{12}$alkyl is unsubstituted or substituted by phenyl, OH, $C_1$–$C_{12}$alkoxy, $C_1$–$C_{12}$alkylsulfonyl, phenylsulfonyl, (4-methylphenyl)sulfonyl and/or by $C_2$–$C_6$alkanoyl;

$R_{11}$ and $R_{12}$ independently of one another are hydrogen, $C_1$–$C_{12}$alkyl which is unsubstituted or substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl; or $R_{11}$ and $R_{12}$ are $C_2$–$C_{12}$alkyl interrupted by one or more —O—, said interrupted $CC_2$–$C_{12}$alkyl is unsubstituted or substituted by OH, $C_1$–$C_4$alkoxy, $C_1$–$C_{12}$alkylsulfonyl, phenylsulfonyl, (4-methylphenyl)sulfonyl and/or $C_1$–$C_6$alkanoyl; or $R_{11}$ and $R_{12}$ are phenyl, $C_2$–$C_6$alkanoyl, benzoyl, $C_1$–$C_6$alkylsulfonyl, phenylsulfonyl, (4-methylphenyl)sulfonyl, naphthylsulfonyl, anthracylsulfonyl or phenanthrylsulfonyl, or $R_{11}$ and $R_{12}$, together with the nitrogen atom to which they are bonded, form a 5-, 6- or 7-membered ring which may be interrupted by —O— or by —$NR_{10}$—;

$R_{13}$ is $C_1$–$C_{12}$alkyl which is unsubstituted or substituted by OH and/or $C_1$–$C_4$alkoxy or $R_{13}$ is $C_2$–$C_{12}$alkyl interrupted by one or more —O—, said interrupted $C_2$–$C_{12}$alkyl is unsubstituted or substituted by OH and/or $C_1$–$C_4$alkoxy;

$R_{14}$ and $R_{15}$ independently of one another are $C_1$–$C_6$alkyl which is unsubstituted or substituted by halogen or phenyl or $R_{14}$ and $R_{15}$ are phenyl which is unsubstituted or substituted by $C_1$–$C_4$alkyl or halogen;

$R_{16}$ and $R_{17}$ independently of one another have one of the meanings of $R_{14}$, or $R_{16}$ and $R_{17}$ together are 1,2-phenylene or $C_2$–$C_6$alkylene which is unsubstituted or substituted by $C_1$–$C_4$alkyl or halogen;

$R_{18}$, $R_{19}$ and $R_{20}$ independently of each other are $C_1$–$C_6$alkyl which is unsubstituted or substituted by halogen; or $R_{18}$, $R_{19}$ and $R_{20}$ are phenyl which is unsubstituted or substituted by $C_1$–$C_4$alkyl or halogen, or $R_{19}$ and $R_{20}$ together are 2,2'-biphenylene or $C_2$–$C_6$alkylene which is unsubstituted or substituted by $C_1$–$C_4$alkyl or halogen;

$R_{21}$, $R_{22}$, $R_{23}$ and $R_{24}$ independently of each other are hydrogen, $C_1$–$C_4$alkyl, halogen, phenyl, $OR_{10}$, $SR_{13}$, $NR_{11}R_{12}$, —S-phenyl, $C_2$–$C_6$alkoxycarbonyl, phenoxycarbonyl, CN, $NO_2$, $C_1$–$C_4$haloalkyl, $S(O)_yC_1$–$C_6$alkyl, $S(O)_yC_6$–$C_{12}$aryl, $C_1$–$C_{12}$alkyl-substituted $S(O)_yC_6$–$C_{12}$aryl, $SO_2O$—$C_1$–$C_6$alkyl, $SO_2O$—$C_6$–$C_{10}$aryl or $NHCONH_2$;

$R_{27}$ and $R_{28}$ independently of one another have one of the meanings given for $R_4$, or $R_{27}$ and $R_{28}$ together are —CO—$NR_{10}$CO—, or —$C(R_{21})$=$C(R_{22})$—$C(R_{23})$=$C(R_{24})$—; and (c) at least one coinitiator.

2. A composition according to claim 1, wherein the compound of formula I, II, III, and IV $R_3$ if x is 1 is $C_1$–$C_{18}$alkylsulfonyl, phenyl-$C_1$–$C_3$alkylsulfonyl, camphorylsulfonyl, C $C_1$–$C_{10}$haloalkylsulfonyl, phenylsulfonyl, naphthylsulfonyl, anthracylsulfonyl or phenanthrylsulfonyl, wherein the groups phenyl, naphthyl, anthracyl and phenanthryl of the radicals phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, $NO_2$, $C_1$–$C_{16}$alkyl, phenyl, $C_1$–$C_4$alkylthio, $OR_{10}$, $COOR_{13}$, $C_1$–$C_4$alkyl-OCO—, $R_{13}OSO_2$— and/or —$NR_{11}R_{12}$; or $R_3$ is a group

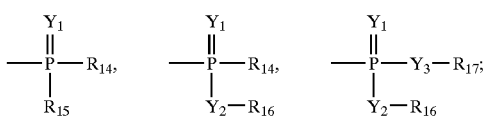

$R_3$ if x is 2 is $C_2$–$C_{12}$alkylenedisulfonyl, phenylenedisulfonyl, naphthylenedisulfonyl,

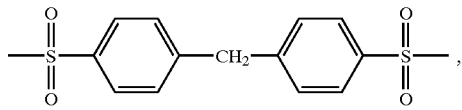

diphenylenedisulfonyl, or oxydiphenylenedisulfonyl, wherein the groups phenylene, naphthylene,

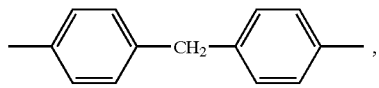

diphenylene and oxydiphenylene of the radicals phenylenedisulfonyl, naphthylenedisulfonyl,

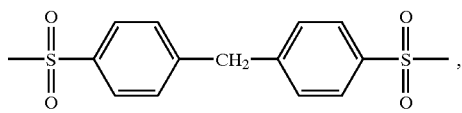

diphenylenedisulfonyl, or oxydiphenylenedisulfonyl are unsubstituted or substituted by $C_1$–$C_{12}$alkyl; and
$Y_1$, $Y_2$ and $Y_3$ independently of each other are —O— or —S—.

3. A composition according to claim 1, wherein component (b) is a compound of formula I, II or III, wherein m is zero.

4. A composition according to claim 1, wherein component (b) is a compound of formula I, III wherein
n and m independently of one another are 0 or 1;
x is 1;
$R_1$ is phenyl which unsubstituted or substituted once or twice by $C_1$–$C_4$alkyl, halogen, $OR_{10}$ or $SR_{13}$;
$R_1'$ is phenylene;
$R_2$ is $C_2$–$C_6$alkoxycarbonyl, or CN;
$R_3$ is $C_1$–$C_8$alkylsulfonyl, or phenylsulfonyl, wherein the group phenyl of the radical phenylsulfonyl is unsubstituted or substituted by $C_1$–$C_8$alkyl or $OR_{10}$; or $R_3$ is a group,

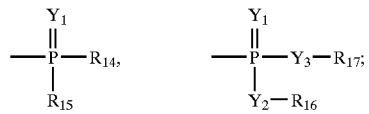

$R_4$ and $R_5$ independently of one another are hydrogen or $C_1$–$C_8$alkyl;
$R_{12}$ is hydrogen or $C_1$–$C_4$alkyl;
$R_{10}$ and $R_{13}$ independently of one another are $C_1$–$C_4$alkyl;
A is —S—;
$Y_1$, $Y_2$ and $Y_3$ are —O—;
$R_{14}$ and $R_{15}$ independently of one another are phenyl or $C_1$–$C_4$alkyl-substituted phenyl;

$R_{16}$ and $R_{17}$ independently of one another are $C_1$–$C_4$alkyl.

5. A photopolymerizable composition according to claim 1, comprising as coinitiator (c) a compound selected from the group consisting of benzophenone derivatives, thioxanthone derivatives or coumarin derivatives.

6. A photopolymerizable composition according to claim 1, comprising additionally at least one binder polymer (d).

7. A photopolymerizable composition according to claim 6, comprising as binder polymer (d), a copolymer of methacrylate and methacrylic acid.

8. A photopolymerizable composition according to claim 1, comprising in addition to the photoinitiator (b) at least one further photoinitiator (e), and/or other additives (f).

9. A photopolymerizable composition according to claim 8, comprising 0.05 to 20% by weight of the photoinitiator (b), or the photoinitiators (b) and (e), based on said composition.

10. A photopolymerizable composition according to claim 1 or 8, comprising 0.05 to 20% by weight of the photoinitiator (b), or the photoinitiators (b) and (e), based on the solid composition.

11. Coated substrate which is coated on at least one surface with a composition according to claim 1.

12. Process for the production of relief images, in which a coated substrate according to claim 11 is subjected to imagewise exposure and then the unexposed portions are removed with a solvent.

13. A process for the radical photopolymerization of compounds containing ethylenically unsaturated double bonds, which comprises irradiating a composition according to claim 1 with electromagnetic radiation in the range from 190 to 600 nm, with e-beam radiation or with X-rays.

14. The use of a composition according to claim 1 for producing pigmented and nonpigmented paints and varnishes, powder coatings, printing inks, printing plates, adhesives, dental compositions, resist materials, including photoresists, color filter materials, as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, and as image recording material, especially for holographic recordings, microelectronic circuits, decolorizing materials, decolorizing materials for image recording materials, for image recording materials using microcapsules.

15. A process according to claim 13 for producing pigmented and non-pigmented paints and varnishes, powder coatings, printing inks, printing plates, adhesives, dental compositions, composite compositions, resists, including photoresists, color filter materials, compositions for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of microlithography, plating, stereolithography, for producing image recording materials, especially for holographic recordings, microelectronic circuits, decoloriozing materials, decolorizing materials for image recording materials, for image recording materials using microcapsules.

* * * * *